(12) United States Patent
Gesing et al.

(10) Patent No.: US 7,625,841 B2
(45) Date of Patent: Dec. 1, 2009

(54) SUBSTITUTED THIENE-3-YLSULPHONYLAMINO(THIO)CARBONYLTRIAZOLIN(ETHI)ONES

(75) Inventors: Ernst Rudolf F. Gesing, Erkrath (DE); Mark Wilhelm Drewes, Langenfeld (DE); Peter Dahmen, Neuss (DE); Dieter Feucht, Kelkheim (DE); Rolf Pontzen, Leichlingen (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 12/157,862

(22) Filed: Jun. 13, 2008

(65) Prior Publication Data

US 2008/0269061 A1    Oct. 30, 2008

Related U.S. Application Data

(62) Division of application No. 10/493,894, filed as application No. PCT/EP02/11743 on Oct. 21, 2002, now Pat. No. 7,410,933.

(30) Foreign Application Priority Data

Nov. 2, 2001 (DE) .................... 101 54 074

(51) Int. Cl.
*A01N 25/00* (2006.01)
*C07D 249/08* (2006.01)
*C07D 333/02* (2006.01)

(52) U.S. Cl. ............... 504/116.1; 548/262.2; 549/29
(58) Field of Classification Search ............ 504/116.1; 548/262.2; 549/29
See application file for complete search history.

(56) References Cited

U.S. PATENT DOCUMENTS

| 4,701,535 | A | 10/1987 | Levitt | 549/60 |
|---|---|---|---|---|
| 5,057,144 | A | 10/1991 | Daum et al. | 71/92 |
| 5,085,684 | A | 2/1992 | Muller et al. | 71/92 |
| 5,094,683 | A | 3/1992 | Daum et al. | 71/94 |
| 5,149,356 | A | 9/1992 | Muller et al. | 71/90 |
| 5,241,074 | A | 8/1993 | Daum et al. | 548/263.8 |
| 5,276,162 | A | 1/1994 | Muller et al. | 548/263.4 |
| 5,300,480 | A | 4/1994 | Haas et al. | 504/193 |
| 5,380,863 | A | 1/1995 | Muller et al. | 548/263.6 |
| 5,405,970 | A | 4/1995 | Daum et al. | 504/193 |
| 5,488,028 | A | 1/1996 | Haas et al. | 504/193 |
| 5,532,378 | A | 7/1996 | Daum et al. | 548/263.8 |
| 5,541,337 | A | 7/1996 | Müller et al. | 548/263.6 |
| 5,554,761 | A | 9/1996 | Haas et al. | 548/263.6 |
| 5,599,944 | A | 2/1997 | Müller et al. | 548/263.6 |
| 5,625,074 | A | 4/1997 | Daum et al. | 548/263.8 |
| 5,631,380 | A | 5/1997 | Haas et al. | 548/263.4 |
| 5,652,372 | A | 7/1997 | Müller et al. | 548/263.4 |
| 5,750,718 | A | 5/1998 | Müller et al. | 548/263.6 |
| 6,383,988 | B1 | 5/2002 | Müller et al. | 504/273 |
| 6,566,536 | B2 | 5/2003 | Müller et al. | 549/65 |
| 6,686,478 | B2 | 2/2004 | Müller et al. | 549/61 |
| 7,410,933 | B2 * | 8/2008 | Gesing et al. | 504/116.1 |
| 2003/0004354 | A1 | 1/2003 | Muller et al. | 98/125 |
| 2003/0171595 | A1 | 9/2003 | Muller et al. | 98/200 |

FOREIGN PATENT DOCUMENTS

| WO | 97/16449 | 5/1997 |
|---|---|---|
| WO | 01/05788 | 1/2001 |

OTHER PUBLICATIONS

J. Org. Chem. 45, (month unavailable) 1980, pp. 617-620, Phillip A. Rossy, Werner Hoffmann, and Norbert Müller, Aromatization of Dihydrothiophenes. Thiophenesaccharin: A Sweet Surprise.

Austr. J. Chem. 48, (month unavailable) 1995, pp. 1907-1916, Scott A. Henderson, Jacqueline O'Connor, Alan R. Rendina, G. Paul Savage and Gregory W. Simpson, "The Synthesis and Biological Activity of 'Crippled Biotin'".

* cited by examiner

*Primary Examiner*—Golam M. M. Shameem
*Assistant Examiner*—Susannah Chung
(74) *Attorney, Agent, or Firm*—Richard E. L. Henderson; Raymond J. Harmuth

(57) ABSTRACT

The invention relates to novel substituted thiene-3-ylsulphonylamino(thio)carbonyl-triazolin(ethi)ones of the formula (I)

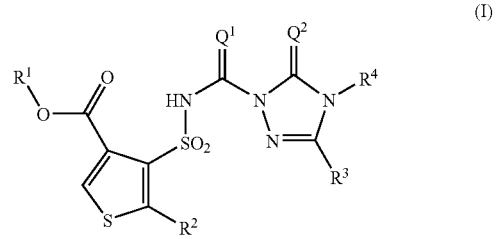

in which $Q^1$, $Q^2$, $R^1$, $R^2$, $R^3$ and $R^4$ are as defined in the disclosure, except for prior-art compounds.

The invention further relates to the preparation of the compounds, to their use as herbicides, and to herbicidal compositions comprising the novel compounds.

12 Claims, No Drawings

SUBSTITUTED THIENE-3-YLSULPHONYLAMINO(THIO)CARBONYLTRIAZOLIN(ETHI)ONES

This application is a division of U.S. application Ser. No. 10/493,894, filed Aug. 16, 2004, now U.S. Pat. No. 7,410,933, which was filed under 35 U.S.C. 371 as a national stage application of PCT/EP02/11743, filed Oct. 21, 2002, which was published in German as International Patent Publication WO 03/037086 on May 8, 2003, which is entitled to the right of priority of German Patent Application 101 54074.4, filed Nov. 2, 2001.

The invention relates to novel substituted thiene-3-ylsulphonylamino(thio)carbonyl-triazolin(ethi)ones, to processes for their preparation and to their use as herbicides.

It is already known that certain substituted thienylsulphonylamino(thio)carbonyl-triazolin(ethi)ones, such as, for example, the compounds methyl 4-[[[(4,5-dihydro-3-ethoxy-4-methyl-5-oxo-1H-1,2,4-triazol-1-yl)carbonyl]amino]sulfonyl]-5-methyl-3-thiophenecarboxylate, methyl 4-[[[(4,5-dihydro-3-methoxy-4-methyl-5-oxo-1H-1,2,4-triazol-1-yl)carbonyl]amino]sulfonyl]-5-methyl-3-thiophenecarboxylate, methyl 4-[[[(4,5-dihydro-4-methyl-5-oxo-3-n-propoxy-1H-1,2,4-triazol-1-yl)carbonyl]amino]sulfonyl]-5-methyl-3-thiophenecarboxylate, methyl 4-[[[(4,5-dihydro-4-methyl-5-oxo-3-isopropoxy-1H-1,2,4-triazol-1-yl)carbonyl]amino]sulfonyl]-5-methyl-3-thiophenecarboxylate, methyl 4-[[[(4-cyclopropyl-4,5-dihydro-3-methoxy-5-oxo-1H-1,2,4-triazol-1-yl)carbonyl]amino]sulfonyl]-5-methyl-3-thiophenecarboxylate, methyl 4-[[[(4-cyclopropyl-4,5-dihydro-3-ethoxy-5-oxo-1H-1,2,4-triazol-1-yl)carbonyl]amino]sulfonyl]-5-methyl-3-thiophenecarboxylate, methyl 4-[[[(4-cyclopropyl-4,5-dihydro-5-oxo-3-n-propoxy-1H-1,2,4-triazol-1-yl)carbonyl]amino]sulfonyl]-5-methyl-3-thiophenecarboxylate, methyl 4-[[[(4-cyclopropyl-4,5-dihydro-5-oxo-3-isopropoxy-1H-1,2,4-triazol-1-yl)carbonyl]amino]sulfonyl]-5-methyl-3-thiophenecarboxylate, methyl 4-[[[(3,4-dicyclopropyl-4,5-dihydro-5-oxo-1H-1,2,4-triazol-1-yl)carbonyl]amino]sulfonyl]-5-methyl-3-thiophenecarboxylate, methyl 4-[[[(4,5-dihydro-3,4-dimethyl-5-oxo-1H-1,2,4-triazol-1-yl)carbonyl]amino]sulfonyl]-5-methyl-3-thiophenecarboxylate, methyl 4-[[[(4,5-dihydro-3-ethyl-4-methyl-5-oxo-1H-1,2,4-triazol-1-yl)carbonyl]amino]sulfonyl]-5-methyl-3-thiophenecarboxylate, methyl 4-[[[(4,5-dihydro-4-methyl-3-methylthio-5-oxo-1H-1,2,4-triazol-1-yl)carbonyl]amino]sulfonyl]-5-methyl-3-thiophenecarboxylate, ethyl 4-[[[(4,5-dihydro-3,4-dimethoxy-5-oxo-1H-1,2,4-triazol-1-yl)carbonyl]amino]sulfonyl]-5-chloro-3-thiophenecarboxylate, methyl 4-[[[(4,5-dihydro-3-ethoxy-4-methyl-5-oxo-1H-1,2,4-triazol-1-yl)thioxocarbonyl]amino]sulfonyl]-5-fluoro-3-thiophenecarboxylate, methyl 4-[[[(4,5-dihydro-3-ethyl-4-methoxy-5-thioxo-1H-1,2,4-triazol-1-yl)carbonyl]amino]sulfonyl]-5-trifluoromethyl-3-thiophenecarboxylate, ethyl 4-[[[(4,5-dihydro-4-ethyl-3-methoxy-5-oxo-1H-1,2,4-triazol-1-yl)carbonyl]-amino]sulfonyl]-5-methyl-3-thiophenecarboxylate and isopropyl 4-[[[(3,4-dimethyl-5-oxo-4,5-dihydro-1H-1,2,4-triazol-1-yl)carbonyl]amino]sulfonyl]-5-ethyl-3-thiophenecarboxylate, have herbicidal properties (cf. WO-A-01/05788, cf. also WO-A-97/16449, WO-A-98/24787). However, the activity of these compounds is not entirely satisfactory.

This invention now provides the novel substituted thiene-3-ylsulphonylamino(thio)-carbonyltriazolin(ethi)ones of the general formula (I)

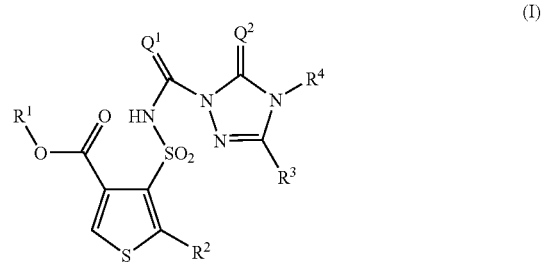

in which
$Q^1$ represents O (oxygen) or S (sulphur),
$Q^2$ represents O (oxygen) or S (sulphur),
$R^1$ represents optionally cyano-, halogen- or $C_1$-$C_4$-alkoxy-substituted alkyl having 1 to 6 carbon atoms, represents in each case optionally cyano- or halogen-substituted alkenyl or alkynyl having in each case 2 to 6 carbon atoms, representing in each case optionally cyano-, halogen- or $C_1$-$C_4$-alkyl-substituted cycloalkyl or cycloalkylalkyl having in each case 3 to 6 carbon atoms in the cycloalkyl group and, if appropriate, 1 to 4 carbon atoms in the alkyl moiety, represents in each case optionally nitro-, cyano-, halogen-, $C_1$-$C_4$-alkyl- or $C_1$-$C_4$-alkoxy-substituted aryl or arylalkyl having in each case 6 or 10 carbon atoms in the aryl group and, if appropriate, 1 to 4 carbon atoms in the alkyl moiety, or represents in each case optionally nitro-, cyano-, halogen-, $C_1$-$C_4$-alkyl- or $C_1$-$C_4$-alkoxy-substituted heterocyclyl or hetero-cyclylalkyl having in each case up to 6 carbon atoms and additionally 1 to 4 nitrogen atoms and/or 1 or 2 oxygen or sulphur atoms in the heterocyclyl group and, if appropriate, 1 to 4 carbon atoms in the alkyl moiety,
$R^2$ represents hydrogen, cyano, nitro, halogen, represents in each case optionally, cyano-, halogen- or $C_1$-$C_4$-alkoxy-substituted alkyl, alkoxy, alkoxycarbonyl, alkylthio, alkylsulfinyl or alkylsulfonyl having in each case 1 to 6 carbon atoms in the alkyl group, or represents in each case optionally cyano- or halogen-substituted alkenyl, alkynyl, alkenyloxy or alkynyloxy having in each case 2 to 6 carbon atoms in the alkenyl or alkynyl group,
$R^3$ represents hydrogen, hydroxyl, mercapto, amino, cyano, halogen, represents optionally cyano-, halogen-, $C_1$-$C_4$-alkoxy-, $C_1$-$C_4$-alkyl-carbonyl- or $C_1$-$C_4$-alkoxy-carbonyl-substituted alkyl having 1 to 6 carbon atoms, represents in each case optionally fluorine-, chlorine- and/or bromine-substituted alkenyl or alkynyl having in each case 2 to 6 carbon atoms, represents in each case optionally cyano-, halogen-, $C_1$-$C_4$-alkoxy- or $C_1$-$C_4$-alkoxy-carbonyl-substituted alkoxy, alkylthio, alkylamino or alkylcarbonylamino having in each case 1 to 6 carbon atoms in the alkyl group, represents alkenyloxy, alkynyloxy, alkenylthio, alkynylthio, alkenylamino or alkynylamino having in each case 3 to 6 carbon atoms in the alkenyl or alkynyl group, represents dialkylamino having in each case 1 to 4 carbon atoms in the alkyl groups, represents in each case optionally methyl- and/or ethyl-substituted aziridino, pyrrolidino, piperidino or morpholino, represents in each case optionally fluorine-, chlorine-, bromine-, cyano- and/or $C_1$-$C_4$-alkyl-substituted cycloalkyl, cycloalkenyl, cycloalkyloxy, cycloalkylthio, cycloalkylamino, cycloalkylalkyl, cycloalkylalkoxy, cycloalkylalkylthio or cycloalkylalkyl-amino having in each case 3 to 6 carbon atoms in the cycloalkyl or cycloalkenyl group and, if appropriate, 1 to 4 carbon atoms in the alkyl moiety, or represents in each case optionally fluorine-, chlorine-, bromine-, cyano-, nitro-, $C_1$-$C_4$-alkyl-, trifluoromethyl-, $C_1$-$C_4$-alkoxy- and/or $C_1$-$C_4$-alkoxy-carbonyl-substituted aryl, arylalkyl, aryloxy, arylalkoxy, arylthio, arylalkylthio, arylamino or arylalkylamino having in each case 6 or 10 carbon atoms in the aryl group and, if appropriate, 1 to 4 carbon atoms in the alkyl moiety, and $R^4$ represents hydrogen, hydroxy, amino, cyano, represents $C_2$-$C_{10}$-alkylideneamino, represents optionally fluorine-, chlorine-, bromine-, cyano-, $C_1$-$C_4$-alkoxy-, $C_1$-$C_4$-alkylcarbonyl- or $C_1$-$C_4$-alkoxy-carbonyl-substituted alkyl having 1 to 6 carbon atoms, represents in each case optionally fluorine-, chlorine- and/or bromine-substituted alkenyl or alkynyl having in each case 2 to 6 carbon atoms, represents in each case optionally fluorine-, chlorine-, bromine-, cyano-, $C_1$-$C_4$-alkoxy- or $C_1$-$C_4$-alkoxy-carbonyl-substituted alkoxy, alkylamino or alkylcarbonylamino having in each case 1 to 6 carbon atoms in the alkyl group, represents alkenyloxy having 3 to 6 carbon atoms, represents dialkylamino having in each case 1 to 4 carbon atoms in the alkyl groups, represents in each case optionally fluorine-, chlorine-, bromine-, cyano- and/or $C_1$-$C_4$-alkyl-substituted cycloalkyl, cycloalkylamino or cycloalkylalkyl having in each case 3 to 6 carbon atoms in the alkyl group and, if appropriate, 1 to 4 carbon atoms in the alkyl moiety, or represents in each case optionally fluorine-, chlorine-, bromine-, cyano-, nitro-, $C_1$-$C_4$-alkyl-, trifluoromethyl- and/or $C_1$-$C_4$-alkoxy-substituted aryl or arylalkyl having in each case 6 or 10 carbon atoms in the aryl group and, if appropriate, 1 to 4 carbon atoms in the alkyl moiety, or together with $R^3$ represents optionally branched and/or $C_1$-$C_4$-alkyl-substituted alkanediyl, oxaalkanediyl, thiaalkanediyl or azaalkanediyl having 3 to 6 carbon atoms, where the oxa, thia or aza components may be positioned at the beginning, at the end or within the alkanediyl grouping, and salts of the compounds of the formula (I)

except for the compounds methyl 4-[[[(4,5-dihydro-3-ethoxy-4-methyl-5-oxo-1H-1,2,4-triazol-1-yl)carbonyl]amino]sulfonyl]-5-methyl-3-thiophenecarboxylate, methyl 4-[[[(4,5-dihydro-3-methoxy-4-methyl-5-oxo-1H-1,2,4-triazol-1-yl)carbonyl]amino]-sulfonyl]-5-methyl-3-thiophenecarboxylate, methyl 4-[[[(4,5-dihydro-4-methyl-5-oxo-3-n-propoxy-1H-1,2,4-triazol-1-yl)carbonyl]amino]sulfonyl]-5-methyl-3-thio-phenecarboxylate, methyl 4-[[[(4,5-dihydro-4-methyl-5-oxo-3-isopropoxy-1H-1,2,4-triazol-1-yl)carbonyl]amino]sulfonyl]-5-methyl-3-thiophenecarboxylate, methyl 4-[[[(4-cyclopropyl-4,5-dihydro-3-methoxy-5-oxo-1H-1,2,4-triazol-1-yl)carbonyl]amino]sulfonyl]-5-methyl-3-thiophenecarboxylate, methyl 4-[[[(4-cyclopropyl-4,5-dihydro-3-ethoxy-5-oxo-1H-1,2,4-triazol-1-yl)carbonyl]amino]sulfonyl]-5-meth-yl-3-thiophenecarboxylate, methyl 4-[[[(4-cyclopropyl-4,5-dihydro-5-oxo-3-n-prop-oxy-1H-1,2,4-triazol-1-yl)carbonyl]amino]sulfonyl]-5-methyl-3-thiophenecarb-oxylate, methyl 4-[[[(4-cyclopropyl-4,5-dihydro-5-oxo-3-isopropoxy-1H-1,2,4-triazol-1-yl)carbonyl]amino]sulfonyl]-5-methyl-3-thiophenecarboxylate, methyl 4-[[[(3,4-dicyclopropyl-4,5-dihydro-5-oxo-1H-1,2,4-triazol-1-yl)carbonyl]amino]-sulfonyl]-5-methyl-3-thiophenecarboxylate, methyl 4-[[[(4,5-dihydro-3,4-dimethyl-5-oxo-1H-1,2,4-triazol-1-yl)carbonyl]amino]sulfonyl]-5-methyl-3-thiophenecarb-oxylate, methyl 4-[[[(4,5-dihydro-3-ethyl-4-methyl-5-oxo-1H-1,2,4-triazol-1-yl)carbonyl]amino]sulfonyl]-5-methyl-3-thiophenecarboxylate, methyl 4-[[[(4,5-dihydro-4-methyl-3-methylthio-5-oxo-1H-1,2,4-triazol-1-yl)carbonyl]amino]sulfonyl]-5-meth-yl-3-thiophenecarboxylate, ethyl 4-[[[(4,5-dihydro-3,4-dimethoxy-5-oxo-1H-1,2,4-triazol-1-yl)carbonyl]amino]sulfonyl]-5-chloro-3-thiophenecarboxylate, methyl 4-[[[(4,5-dihydro-3-ethoxy-4-methyl-5-oxo-1H-1,2,4-triazol-1-yl)thioxocarbonyl]-amino]sulfonyl]-5-fluoro-3-thiophenecarboxylate, methyl 4-[[[(4,5-dihydro-3-ethyl-4-methoxy-5-thioxo-1H-1,2,4-triazol-1-yl)carbonyl]amino]sulfonyl]-5-trifluoro-methyl-3-thiophenecarboxylate, ethyl 4-[[[(4,5-dihydro-4-ethyl-3-methoxy-5-oxo-1H-1,2,4-triazol-1-yl)carbonyl]amino]sulfonyl]-5-methyl-3-thiophenecarboxylate and isopropyl 4-[[[(3,4-dimethyl-5-oxo-4,5-dihydro-1H-1,2,4-triazol-1-yl)carbonyl]amino]sulfonyl]-5-ethyl-3-thiophenecarboxylate known from WO-A-01/05788, which are excluded by disclaimer.

Saturated or unsaturated hydrocarbon groupings, such as alkyl, allkanediyl, alkenyl or alkynyl, are in each case straight-chain or branched as far as this is possible—including in combinations with heteroatoms, such as in alkoxy.

Optionally substituted radicals can be mono- or polysubstituted, and in the case of polysubstitution, the substituents can be identical or different.

Preferred substituents or ranges of the radicals present in the formulae listed above and below are defined below.

$Q^1$ preferably represents O (oxygen) or S (sulphur).

$Q^2$ preferably represents O (oxygen) or S (sulphur).

$R^1$ preferably represents in each case optionally cyano-, fluorine-, chlorine-, methoxy- or ethoxy-substituted methyl, ethyl, n- or isoproyl, n-, iso-, s- or t-butyl, represents in each case optionally cyano-, fluorine- or chlorine-substituted propenyl, butenyl, propynyl or butynyl, represents in each case optionally cyano-, fluorine-, chlorine-, methyl- or ethyl-substituted cyclopropyl, cyclobutyl, cyclopentyl, cyclohexyl, cyclopropylmethyl, cyclobutyl-methyl, cyclopentylmethyl or cyclohexylmethyl, represents in each case optionally cyano-, fluorine-, chlorine-, methyl-, ethyl-, n- or isopropyl-, trifluoromethyl-, methoxy-, ethoxy-, n- or isopropoxy-, difluoromethoxy- or trifluoromethoxy-substituted phenyl, phenylmethyl or phenylethyl, or represents in each case optionally cyano-, fluorine-, chlorine-, bromine-, methyl-, ethyl-, n- or isopropyl-, methoxy-, ethoxy-, n- or isopropoxy-substituted heterocyclyl or heterocyclylmethyl, where the heterocyclyl group is in each case selected from the group consisting of oxetanyl, thietanyl, furyl, tetrahydrofuryl, thienyl, tetrahydrothienyl.

$R^2$ preferably represents hydrogen, cyano, fluorine, chlorine, bromine, represents in each case optionally cyano-, fluorine-, chlorine-, methoxy- or ethoxy-substituted methyl, ethyl, n- or isopropyl, n-, iso-, s- or t-butyl, methoxy, ethoxy, n- or isopropoxy, methoxycarbonyl, ethoxycarbonyl, n- or isopropoxycarbonyl, methylthio, ethylthio, n- or isopropylthio, methylsulfinyl, ethylsulfinyl, methylsulfonyl or ethylsulfonyl, or represents in each case optionally cyano-, fluorine- or chlorine-substituted propenyl, butenyl, propynyl, butynyl, propenyloxy, butenyloxy, propynyloxy or butynyloxy.

$R^3$ preferably represents hydrogen, hydroxy, mercapto, amino, cyano, fluorine, chlorine, bromine, represents in each case optionally fluorine-, chlorine-, cyano-, methoxy-, ethoxy-, n- or isopropoxy-, acetyl-, propionyl-, n- or isobutyroyl-, methoxycarbonyl-, ethoxycarbonyl-, n- or isopropoxycarbonyl-substituted methyl, ethyl, n- or isopropyl, n-, iso-, s- or t-butyl, n-, iso-, s- or t-pentyl or neopentyl, represents in each case optionally fluorine-, chlorine- and/or bromine-substituted ethenyl, propenyl, butenyl, ethynyl, propynyl or butynyl, represents in each case optionally fluorine-, chlorine-, cyano-, methoxy-, ethoxy-, n- or isopropoxy-, n-, iso-, s- or t-butoxy-, methoxycarbonyl-, ethoxycarbonyl-, n- or isopropoxycarbonyl-substituted methoxy, ethoxy, n- or isopropoxy, n-, iso-, s- or t-butoxy, n-, iso-, s- or t-pentyloxy or neopentyloxy, methylthio, ethylthio, n- or isopropylthio, n-, iso-, s- or t-butylthio, methylamino, ethylamino, n- or isopropylamino, n-, iso-, s- or t-butylamino, acetylamino or propionylamino, represents propenyloxy, butenyloxy, ethynyloxy, propynyloxy, butynyloxy, propenylthio, butenylthio, propynylthio, butynythio, propenylamino, butenylamino, propynylamino or butynylamino, represents dimethylamino, diethylamino or dipropylamino, represents in each case optionally fluorine-, chlorine-, methyl- and/or ethyl-substituted cyclopropyl, cyclobutyl, cyclopentyl, cyclohexyl, cyclopentenyl, cyclohexenyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents in each case optionally fluorine-, chlorine-, bromine-, methyl-, trifluoromethyl-, methoxy- or methoxycarbonyl-substituted phenyl, benzyl, phenoxy, benzyloxy, phenylthio, benzylthio, phenylamino or benzylamino.

$R^4$ preferably represents hydrogen, hydroxy, amino, represents in each case optionally fluorine-, chlorine-, cyano-, methoxy- or ethoxy-substituted methyl, ethyl, n- or isopropyl, n-, iso-, s- or t-butyl, represents in each case optionally fluorine-, chlorine- and/or bromine-substituted ethenyl, propenyl, butenyl, propynyl or butynyl, represents in each case optionally fluorine-, chlorine-, cyano-, methoxy- or ethoxy-substituted methoxy, ethoxy, n- or isopropoxy, n-, iso-, s- or t-butoxy, methylamino, ethylamino, n- or isopropylamino, n-, iso-, s- or t-butylamino, represents propenyloxy or butenyloxy, represents dimethylamino or diethylamino, represents in each case optionally fluorine-, chlorine-, methyl- and/or ethyl-substituted cyclopropyl, cyclobutyl, cyclopentyl, cyclohexyl, cyclopropylamino, cyclobutylamino, cyclopentylamino, cyclohexylamino, cyclopropylmethyl, cyclobutylmethyl, cyclopentylmethyl or cyclohexylmethyl, or represents in each case optionally fluorine-, chlorine-, methyl-, trifluoromethyl- and/or methoxy-substituted phenyl or benzyl.

$R^3$ and $R^4$ together preferably represent trimethylene (propane-1,3-diyl), 1-oxatrimethylene, 1-thiatrimethylene, 1-azatrimethylene, tetramethylene (butane-1,4-diyl), 1-oxatetramethylene, 1-thiatetramethylene, 1-azatetramethylene or pentamethylene (pentane-1,5-diyl), each of which is optionally mono- to trisubstituted by methyl and/or ethyl, where the position 1 is connected to the point of attachment of $R^3$.

$Q^1$ particularly preferably represents O (oxygen) or S (sulphur).

$Q^2$ particularly preferably represents O (oxygen) or S (sulphur).

$R^1$ particularly preferably represents in each case optionally fluorine-, chlorine-, methoxy- or ethoxy-substituted methyl, ethyl, n- or isopropyl.

$R^2$ particularly preferably represents fluorine, chlorine, bromine or represents in each case optionally fluorine-, chlorine-, methoxy- or ethoxy-substituted methyl, ethyl, n- or isopropyl.

$R^3$ particularly preferably represents hydrogen, chlorine, bromine, represents in each case optionally fluorine-, chlorine-, methoxy-, ethoxy-, n- or isopropoxy-substituted methyl, ethyl, n- or isopropyl, n-, iso-, s- or t-butyl, n-, iso-, s- or t-pentyl or neopentyl, represents in each case optionally fluorine- or chlorine-substituted ethenyl, propenyl, butenyl, propynyl or butynyl, represents in each case optionally fluorine-, chlorine-, methoxy-, ethoxy-, n- or isopropoxy-substituted methoxy, ethoxy, n- or isopropoxy, n-, iso-, s- or t-butoxy, n-, iso-, s- or t-pentyloxy, neopentyloxy, methylthio, ethylthio, n- or isopropylthio, n-, iso-, s- or t-butylthio, methylamino, ethylamino, n- or isopropylamino, represents propenyloxy, propynyloxy, propenylthio, propynylthio, propenylamino or propynylamino, represents dimethylamino or diethylamino, represents in each case optionally fluorine-, chlorine- or methyl-substituted cyclopropyl, cyclopropyloxy, cyclopropylmethyl, cyclopropylmethoxy, cyclobutyloxy, cyclopentyloxy or cyclohexyloxy, or represents in each case optionally fluorine-, chlorine- or methyl-substituted phenoxy or benzyloxy.

$R^4$ particularly preferably represents in each case optionally fluorine-, chlorine-, methoxy- or ethoxy-substituted methyl, ethyl, n- or isopropyl, represents in each case optionally fluorine- or chlorine-substituted ethenyl, propenyl or propynyl, represents in each case optionally fluorine-, chlorine-, methoxy- or ethoxy-substituted methoxy, ethoxy, n- or isopropoxy, represents methyl-amino, or represents cyclopropyl.

$R^3$ and $R^4$ together particularly preferably represent trimethylene (propane-1,3-diyl), 1-oxatrimethylene, 1-thiatrimethylene, 1-azatrimethylene, tetramethylene (butane-1,4-diyl), 1-oxatetramethylene, 1-thiatetramethylene, 1-azatetramethylene or pentamethylene (pentane-1,5-diyl), each of which is optionally mono- or disubstituted by methyl, where the position 1 is connected to the point of attachment of $R^3$.

The invention preferably also provides the sodium, potassium, lithium, magnesium, calcium, ammonium, $C_1$-$C_4$-alkylammonium, (where the alkyl radical is optionally substituted by hydroxyl), di($C_1$-$C_4$-alkyl)ammonium, tri($C_1$-$C_4$-alkyl)ammonium, tetra($C_1$-$C_4$-alkyl)ammonium, tri($C_1$-$C_4$-alkyl)sulfonium, $C_5$- or $C_6$-cyclo-alkylammonium and di($C_1$-$C_2$-alkyl)benzylammonium salt and also the di($C_1$-$C_2$-alkyl) pyridinylammonium salts and the pyrrolidinium salts of compounds of the formula (I) in which $Q^1$, $Q^2$, $R^1$, $R^2$, $R^3$ and $R^4$ have the meanings given above as being preferred.

A very particularly preferred group are those compounds of formula (I) in which $R^1$ represents methyl and $Q^1$ and $Q^2$ and $R^2$, $R^3$ and $R^4$ have the meanings given above as being particularly preferred, except for the prior-art compounds methyl 4-[[[(4,5-dihydro-3-ethoxy-4-methyl-5-oxo-1H-1,2,4-triazol-1-yl)carbonyl]amino]sulfonyl]-5-methyl-3-thiophenecarboxyl-ate, methyl 4-[[[(4,5-dihydro-3-methoxy-4-methyl-5-oxo-1H-1,2,4-triazol-1-yl)carbonyl]amino]sulfonyl]-5-methyl-3-thiophenecarboxylate, methyl 4-[[[(4,5-dihydro-4-methyl-5-oxo-3-n-propoxy-1H-1,2,4-triazol-1-yl)carbonyl]amino]sulfonyl]-5-methyl-3-thiophenecarboxylate, methyl 4-[[[(4,5-dihydro-4-methyl-5-oxo-3-isopropoxy-1H-1,2,4-triazol-1-yl)carbonyl]amino]sulfonyl]-5-methyl-3-thiophenecarboxylate, methyl 4-[[[(4-cyclopropyl-4,5-dihydro-3-methoxy-5-oxo-1H-1,2,4-triazol-1-yl)carbonyl]amino]sulfonyl]-5-methyl-3-thiophenecarboxylate, methyl 4-[[[(4-cyclopropyl-4,5-dihydro-3-ethoxy-5-oxo-1H-1,2,4-triazol-1-yl)carbonyl]amino]sulfonyl]-5-methyl-3- thiophenecarboxylate, methyl 4-[[[(4-cyclopropyl-4,5-dihydro-5-oxo-3-n-propoxy-1H-1,2,4-triazol-1-yl)carbonyl]amino]sulfonyl]-5-methyl-3-thiophenecarboxylate, methyl 4-[[[(4-cyclopropyl-4,5-dihydro-5-oxo-3-isopropoxy-1H-1,2,4-triazol-1-yl)carbonyl]amino]sulfonyl]-5-methyl-3-thiophenecarboxylate, methyl 4-[[[(3,4-di-cyclopropyl-4,5-dihydro-5-oxo-1H-1,2,4-triazol-1-yl)carbonyl]amino]sulfonyl]-5-methyl-3-thiophenecarboxylate, methyl 4-[[[(4,5-dihydro-3,4-dimethyl-5-oxo-1H-1,2,4-triazol-1-yl)carbonyl]amino]sulfonyl]-5-methyl-3-thiophenecarboxylate, methyl 4-[[[(4,5-dihydro-3-ethyl-4-methyl-5-oxo-1H-1,2,4-triazol-1-yl)carbonyl]amino]sulfonyl]-5-methyl-3-thiophenecarboxylate, methyl 4-[[[(4,5-dihydro-4-methyl-3-methyl-thio-5-oxo-1H-1,2,4-triazol-1-yl)carbonyl]amino]sulfonyl]-5-methyl-3-thiophenecarboxylate, methyl 4-[[[(4,5-dihydro-3-ethoxy-4-methyl-5-oxo-1H-1,2,4-triazol-1-yl)thioxocarbonyl]amino]sulfonyl]-5-fluoro-3-thiophenecarboxylate and methyl 4-[[[(4,5-dihydro-3-ethyl -4-methoxy-5-thioxo-1H-1,2,4-triazol-1-yl)carbonyl]amino]sulfonyl]-5-trifluoromethyl-3-thiophenecarboxylate.

A further very particularly preferred group are those compounds of the formula (I) in which
$R^1$ represents ethyl and $Q^1$ and $Q^2$ and $R^2$, $R^3$ and $R^4$ have the meanings given above as being particularly preferred, except for the prior-art compounds ethyl 4-[[[(4,5-dihydro-3,4-dimethoxy-5-oxo-1H-1,2,4-triazol-1-yl)carbonyl]amino]sulfonyl]-5-chloro-3-thiophenecarboxylate and ethyl 4-[[[(4,5-dihydro-4-ethyl-3-methoxy-5-oxo-1H-1,2,4-triazol-1-yl)carbonyl]-amino]sulfonyl]-5-methyl-3-thiophenecarboxylate.

A further very particularly preferred group are those compounds of the formula (I) in which
$R^1$ represents n-propyl and $Q^1$ and $Q^2$ and $R^2$, $R^3$ and $R^4$ have the meanings given above as being particularly preferred.

A further very particularly preferred group are those compounds of the formula (I) in which
$R^1$ represents isopropyl and $Q^1$ and $Q^2$ and $R^2$, $R^3$ and $R^4$ have the meanings given above as being particularly preferred, except for the prior-art compound isopropyl 4-[[[(3,4-dimethyl-5-oxo-4,5-dihydro-1H-1,2,4-triazol-1-yl)carbonyl]amino]sulfonyl]-5-ethyl-3-thiophenecarboxylate.

A further very particularly preferred group are those compounds of the formula (I) in which
$Q^1$ and $Q^2$ and $R^1$ and $R^2$ have the meanings given above as being particularly preferred and $R^3$ and $R^4$ together represent trimethylene (propane-1,3-diyl), 1-oxatrimethylene, 1-thiatrimethylene, 1-azatrimethylene, tetramethylene (butane-1,4-diyl), 1-oxatetramethylene, 1-thiatetramethylene, 1-azatetramethylene or pentamethylene (pentane-1,5-diyl), each of which is optionally mono- or disubstituted by methyl, where the position 1 is connected to the point of attachment of $R^3$.

Further groups which may be particularly emphasized are:

Group 1:
Compounds in which $R^3$ represents halogen- or $C_1$-$C_4$-alkoxy-substituted alkoxy having 1 to 6 carbon atoms.

Group 2:
Compounds in which $R^3$ represents optionally methyl- and/or ethyl-substituted cycloalkoxy having 3 to 6 carbon atoms.

Group 3:
Compounds in which $R^3$ represents optionally fluorine-, chlorine-, bromine-, methyl-, trifluoromethyl-, methoxy- or methoxycarbonyl-substituted phenoxy or benzyloxy.

The abovementioned general or preferred radical definitions apply both to the end products of the formula (I) and, correspondingly, to the starting materials or intermediates required in each case for the preparation. These radical definitions can be combined with one another as desired, i.e. including combinations between the given preferred ranges.

Preference according to the invention is given to those compounds of the formula (I) which contain a combination of the meanings listed above as being preferred.

Particular preference according to the invention is given to those compounds of the formula (I) which contain a combination of the meanings listed above as being particularly preferred.

Very particular preference according to the invention is given to those compounds of the formula (I) which contain a combination of the meanings listed above as being very particularly preferred.

The novel substituted thien-3-yl sulphonylamino(thio)carbonyl triazolin(ethi)ones of the general formula (I) have interesting biological properties. In particular, they have strong herbicidal activity.

The novel substituted thien-3-yl sulphonylamino(thio)carbonyl triazolin(ethi)ones of the general formula (1) are obtained when (a) substituted thiophene-3-sulphonamides of the general formula (II)

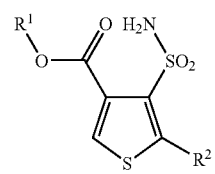

(II)

in which
$R^1$ and $R^2$ are as defined above,
are reacted with substituted triazolin(ethi)ones of the general formula (III)

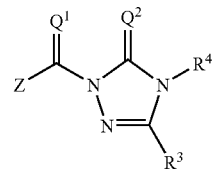

(III)

in which
$Q^1$, $Q^2$, $R^3$ and $R^4$ are as defined above and
Z represents halogen, alkoxy, aryloxy or arylalkoxy,
if appropriate in the presence of a reaction auxiliary and if appropriate in the presence of a diluent,
or when (b) substituted thien-3-yl sulphonyl iso(thio)cyanates of the general formula (IV)

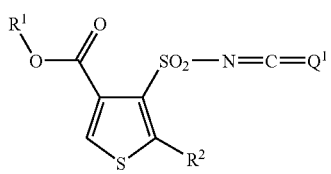

(IV)

in which
Q¹, R¹ and R² are as defined above,
are reacted with triazolin(ethi)ones of the general formula (V)

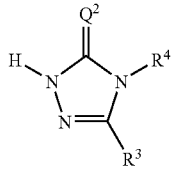

(V)

in which
Q², R⁴ and R⁵ are as defined above,
if appropriate in the presence of a reaction auxiliary and if appropriate in the presence of a diluent,
or when (c) substituted thiophene-3-sulphonyl chlorides of the general formula (VI)

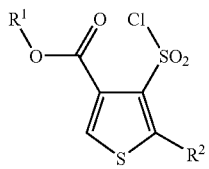

(VI)

in which
R¹ and R² are as defined above,
are reacted with triazolin(ethi)ones of the general formula (V)

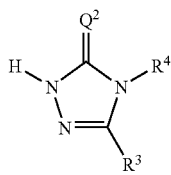

(V)

in which
Q², R⁴ and R⁵ are as defined above,
and metal (thio)cyanates of the general formula (VII)

M-Q¹-CN  (VII)

in which
Q¹ is as defined above,
if appropriate in the presence of a reaction auxiliary and if appropriate in the presence of a diluent,
or when (d) substituted thiophene-3-sulphonyl chlorides of the general formula (VI)

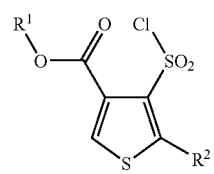

(VI)

in which
R¹ and R² are as defined above,
are reacted with triazolin(ethi)one (thio)carboxamides of the general formula (VIII)

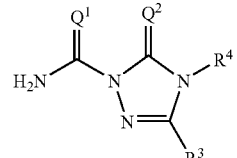

(VIII)

in which
Q¹, Q², R³ and R⁴ are as defined above,
if appropriate in the presence of a reaction auxiliary and if appropriate in the presence of a diluent,
or when (e) substituted thien-3-yl sulphonylamino(thio)carbonyl compounds of the general formula (IX)

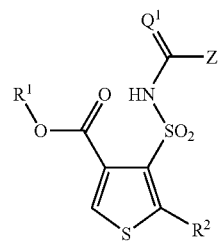

(IX)

in which
Q¹, R¹ and R² are as defined above and
Z represents halogen, alkoxy, aryloxy or arylalkoxy,
are reacted with triazolin(ethi)ones of the general formula (V)

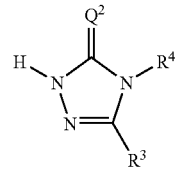

(V)

in which

Q², R⁴ and R⁵ are each as defined above, if appropriate in the presence of a reaction auxiliary and if appropriate in the presence of a diluent, and the compounds of the formula (I) obtained by the processes (a), (b), (c), (d) or (e) are, if appropriate, converted by customary methods into salts.

Using, for example, 2-bromo-4-ethoxycarbonyl thiophene-3-sulphonamide and 4,5-dimethoxy-2-phenoxycarbonyl-2,4-dihydro-3H-1,2,4-triazol-3-one as starting materials, the course of the reaction in the process (a) according to the invention can be illustrated by the following formula scheme:

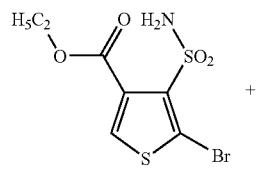

Using, for example, 2-dichloromethyl-4-methoxycarbonyl thien-3-yl-sulphonyl isothiocyanate and 5-ethoxy-4-methyl-2,4-dihydro-3H-1,2,4-triazol-3-one as starting materials, the course of the reaction in the process (b) according to the invention can be illustrated by the following formula scheme:

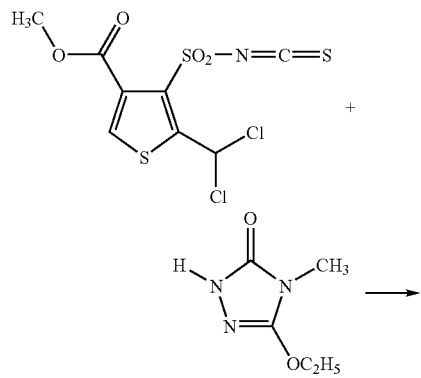

-continued

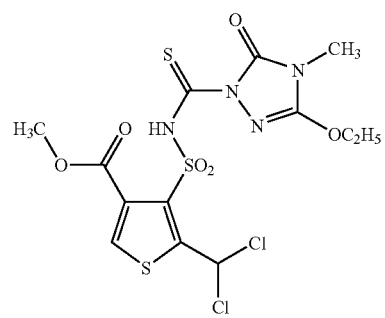

Using, for example, 4-ethoxycarbonyl-2-ethyl thiophene-3-sulphonyl chloride, 5-ethyl-4-methoxy-2,4-dihydro-3H-1,2,4-triazole-3-thione and potassium cyanate as starting materials, the course of the reaction in the process (c) according to the invention can be illustrated by the following formula scheme:

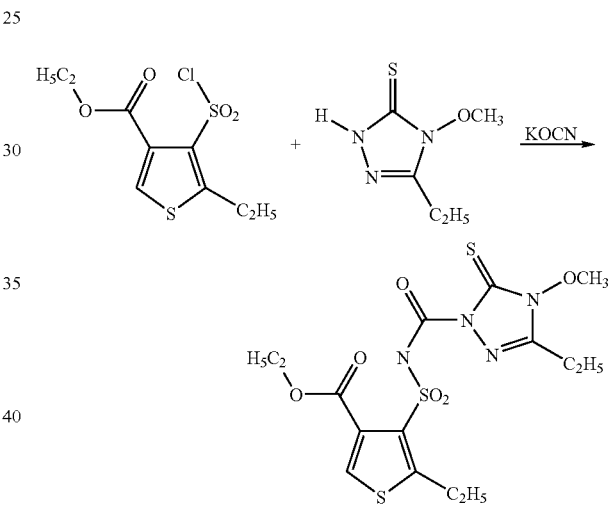

Using, for example, 4-ethoxycarbonyl-2-trifluoromethyl thiophene-3-sulphonyl chloride and 4-ethyl-5-methoxy-2,4-dihydro-3H-1,2,4-triazol-3-one-2-carboxamide as starting materials, the course of the reaction in the process (d) according to the invention can be illustrated by the following formula scheme:

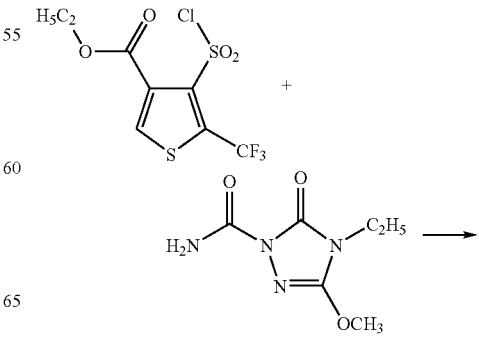

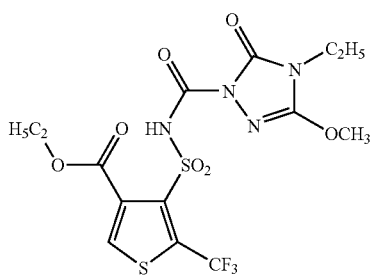

Using, for example, O-methyl N-(2-ethyl-4-isopropoxycarbonyl thien-3-yl-sulphonyl)urethane and 4,5-dimethyl-2,4-dihydro-3H-1,2,4-triazol-3-one as starting materials, the course of the reaction in the process (e) according to the invention can be illustrated by the following formula scheme:

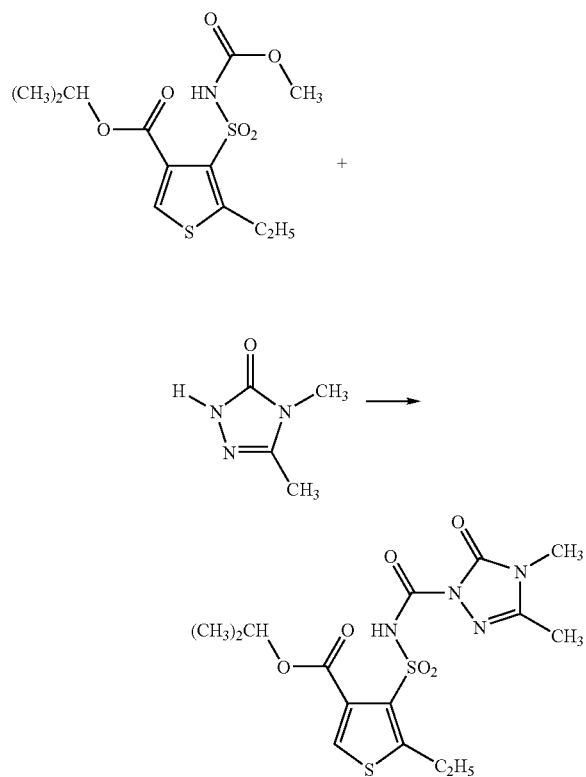

The formula (II) provides a general definition of the substituted thiophene-3-sulphonamides to be used as starting materials in the process (a) according to the invention for preparing compounds of the general formula (I). In the general formula (II), $R^1$ and $R^2$ preferably or in particular have those meanings which have already been mentioned above, in connection with the description of the compounds of the general formula (I) according to the invention, as being preferred or particularly preferred for $R^1$ and $R^2$.

The substituted thiophene-3-sulphonamides of the general formula (II) are known and/or can be prepared by processes known per se (cf. J. Org. Chem. 45 (1980), 617-620, WO-A-01/05788).

The substituted thiophene-3-sulphonamides of the general formula (II) are obtained when substituted thiophene-3-sulphonyl chlorides of the general formula (VI)

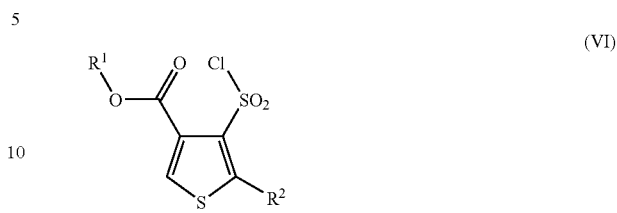

in which $R^1$ and $R^2$ are as defined above, are reacted with ammonia or ammonium salts, such as, for example, ammonium acetate or ammonium carbonate, if appropriate in the presence of a diluent, such as, for example, water or methylene chloride, at temperatures between 0° C. and 100° C.

The formula (III) provides a general definition of the substituted triazolin(ethi)ones furthermore to be used as starting materials in the process (a) according to the invention for preparing compounds of the general formula (I). In the general formula (III), $Q^1$, $Q^2$, $R^3$ and $R^4$ preferably or in particular have those meanings which have already been mentioned above, in connection with the description of the compounds of the general formula (I) according to the invention, as being preferred or particularly preferred for $Q^1$, $Q^2$, $R^3$ and $R^4$.

The starting materials of the general formula (III) are known and/or can be prepared by processes known per se (cf EP-A-341 489, EP-A-422 469, EP-A-425 948, EP-A-431 291, EP-A-507 171, EP-A-534 266).

The formula (IV) provides a general definition of the substituted thien-3-yl sulphonyl iso(thio)cyanates to be used as starting materials in the process (b) according to the invention for preparing compounds of the general formula (I). In the general formula (IV), $Q^1$, $R^1$ and $R^2$ preferably or in particular have those meanings which have already been mentioned above, in connection with the description of the compounds of the general formula (I) according to the invention, as being preferred or particularly preferred for $Q^1$, $R^1$ and $R^2$.

The starting materials of the general formula (IV) are known and/or can be prepared by processes known per se (cf. U.S. Pat. No. 4,701,535).

The formula (V) provides a general definition of the triazolin(ethi)ones to be used as starting materials in the processes (b), (c) and (e) according to the invention for preparing compounds of the general formula (I). In the general formula (V), $Q^2$, $R^4$ and $R^5$ preferably or in particular have those meanings which have already been mentioned above, in connection with the description of the compounds of the general formula (I) according to the invention, as being preferred or particularly preferred for $Q^2$, $R^4$ and $R^5$.

The starting materials of the general formula (V) are known and/or can be prepared by processes known per se (cf. EP-A-341 489, EP-A-422 469, EP-A-425 948, EP-A-431 291, EP-A-507 171, EP-A-534 266).

The formula (VI) provides a general definition of the substituted thiophene-3-sulphonyl chlorides to be used as starting materials in the processes (c) and (d) according to the invention for preparing compounds of the general formula (I). In the general formula (VI), $R^1$ and $R^2$ preferably or in particular have those meanings which have already been mentioned above, in connection with the description of the compounds of the general formula (I) according to the invention, as being preferred or particularly preferred for $R^1$ and $R^2$.

The substituted thiophene-3-sulphonyl chlorides of the general formula (VI) are known and/or can be prepared by processes known per se (cf. J. Org. Chem. 45 (1980), 617-620, WO-A-01/05788).

The substituted thiophene-3-sulphonyl chlorides of the general formula (VI) are obtained when 3-amino-thiophene-4-carboxylic esters of the general formula (X)

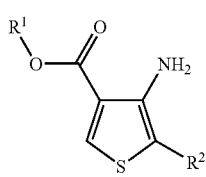
(X)

in which
$R^1$ and $R^2$ are as defined above,
or acid adducts of compounds of the formula (X), such as, for example, the hydrochlorides—
are reacted with an alkali metal nitrite, such as, for example, sodium nitrite, in the presence of hydrochloric acid at temperatures between −10° C. and +10° C., and the resulting diazonium salt solution is reacted with sulphur dioxide in the presence of a diluent, such as, for example, dichloromethane, 1,2-dichloroethane or acetic acid, and in the presence of a catalyst, such as, for example, copper(I) chloride and/or copper(II) chloride, at temperatures between −10° C. and +50° C.

The intermediates of the general formula (X) are known and/or can be prepared by processes known per se (cf. Austr. J. Chem. 48 (1995), 1907-1916; Preparation Examples).

The formula (VIII) provides a general definition of the triazolin(ethi)one (thio)-carboxamides to be used as starting materials in the process (d) according to the invention for preparing compounds of the general formula (I). In the general formula (VIII), $Q^1$, $Q^2$, $R^3$ and $R^4$ preferably or in particular have those meanings which have already been mentioned above, in connection with the description of the compounds of the general formula (I) according to the invention, as being preferred or particularly preferred for $Q^1$, $Q^2$, $R^3$ and $R^4$.

The starting materials of the general formula (VIII) are known and/or can be prepared by processes known per se.

The formula (IX) provides a general definition of the substituted thien-3-yl-sulphonylamino(thio)carbonyl compounds to be used as starting materials in the process (e) according to the invention for preparing compounds of the general formula (I). In the general formula (IX), $Q^1$, $R^1$ and $R^2$ preferably or in particular have those meanings which have already been mentioned above, in connection with the description of the compounds of the general formula (I) according to the invention, as being preferred or particularly preferred for $Q^1$, $R^1$ and $R^2$.

The starting materials of the general formula (IX) are known and/or can be prepared by processes known per se.

The processes (a), (b), (c), (d) and (e) according to the invention for preparing the novel compounds of the formula (I) are preferably carried out using diluents. Suitable diluents are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and also dimethyl sulphoxide, tetramethylene sulphone and hexamethylphosphoric triamide.

Reaction auxiliaries suitable for the processes (a), (b), (c), (d) and (e) according to the invention are all acid binders which are customarily used for such reactions.

Preference is given to alkali metal hydroxides, such as, for example, sodium hydroxide and potassium hydroxide, alkaline earth metal hydroxides, such as, for example, calcium hydroxide, alkali metal carbonates and alkoxides, such as sodium carbonate and potassium carbonate, sodium tert-butoxide and potassium tert-butoxide, furthermore basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4.3.0]-non-5-ene (DBN), 1,8-diazabicyclo-[5.4.0]-undec-7-ene (DBU) and 1,4-diazabicyclo[2.2.2]-octane (DABCO).

The reaction temperatures in the processes (a), (b), (c), (d) and (e) according to the invention can be varied within a relatively wide range. In general, the processes are carried out at temperatures between −20° C. and +150° C., preferably at temperatures between 0° C. and +100° C.

The processes (a), (b), (c), (d) and (e) according to the invention are generally carried out under atmospheric pressure. However, it is also possible to operate under elevated or reduced pressure.

For carrying out the processes (a), (b), (c), (d) and (e) according to the invention, the starting materials required in each case are generally employed in approximately equimolar amounts. However, it is also possible to use a relatively large excess of one of the components used in each case. The reactions are generally carried out in a suitable diluent in the presence of an acid acceptor, and the reaction mixture is stirred for several hours at the temperature required in each case. Work-up in the processes (a), (b), (c), (d) and (e) according to the invention is in each case carried out by customary methods (cf. the Preparation Examples).

If appropriate, salts can be prepared from the compounds of the general formula (I) according to the invention. Such salts are obtained in a simple manner by customary methods for forming salts, for example by dissolving or dispersing a compound of the formula (I) in a suitable solvent, such as, for example, methylene chloride, acetone, tert-butyl methyl ether or toluene, and adding a suitable base. The salts can then—if appropriate after prolonged stirring—be isolated by concentration or filtration with suction.

The active compounds according to the invention can be used as defoliants, desiccants, haulm killers and, especially, as weedkillers. Weeds in the broadest sense are to be understood as meaning all plants which grow in locations where they are not wanted. Whether the substances according to the invention act as total or selective herbicides depends essentially on the amount used.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but also extends in the same manner to other plants.

Depending on the concentration, the active compounds according to the invention are suitable for total weed control, for example on industrial sites and rail tracks and on paths and areas with or without tree growth. Equally, the compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The compounds of the formula (I) according to the invention have strong herbicidal activity and a broad activity spectrum when applied on the soil and on above-ground parts of plants. To a certain extent, they are also suitable for selective control of monocotyledonous and dicotyledonous weeds in monocotyledonous and dicotyledonous crops, both by the pre-emergence and by the post-emergence method.

At certain concentrations or application rates, the active compounds according to the invention can also be used for controlling animal pests and fungal or bacterial plant diseases. If appropriate, they can also be employed as intermediates or precursors for the synthesis of further active compounds.

According to the invention, it is possible to treat all plants and parts of plants. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including transgenic plants and including plant varieties which may or may not be protectable by plant variety property rights. Parts of plants are to be understood as meaning all above-ground and below-ground parts and organs of plants, such as shoot, leaf, flower and root, examples which may be mentioned being leaves, needles, stems, trunks, flowers, fruit bodies, fruits and seeds and also roots, tubers and rhizomes. Plant parts also include harvested goods and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation materials, in particular in the case of seeds, furthermore by single- or multi-layer coating.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use dyestuffs, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 percent by weight of active compound, preferably between 0.5 and 90%.

For controlling weeds, the active compounds according to the invention, as such or in the form of their formulations, can also be used as mixtures with known herbicides and/or with crop-plant compatibility-improving substances ("safeners"), finished formulations or tank mixes being possible. Also possible are mixtures with weedkillers comprising one or more known herbicides and a safener.

Possible components for the mixtures are known herbicides, for example acetochlor, acifluorfen(-sodium), aclonifen, alachlor, alloxydim(-sodium), ametryne, amicarbazone, amidochlor, amidosulfuron, anilofos, asulam, atrazine, azafenidin, azimsulfuron, beflubutamide, benazolin(-ethyl), benfuresate, bensulfuron(-methyl), bentazone, benzfendizone, benzobicyclon, benzofenap, benzoylprop(-ethyl), bialaphos, bifenox, bispyribac(-sodium), bromobutide, bromofenoxim, bromoxynil, butachlor, butafenacil(-allyl), butroxydim, butylate, cafenstrole, caloxydim, carbetamide, carfentrazone(-ethyl), chlomethoxyfen, chloramben, chloridazon, chlorimuron(-ethyl), chlomitrofen, chlorsulfuron, chlorotoluron, cinidon(-ethyl), cinmethylin, cinosulfuron, clefoxydim, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, dichloroprop(-P), diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, eproprodan, EPTC, esprocarb, ethalfluralin, ethametsulfuron(-methyl), ethofumesate, ethoxyfen, ethoxysulfuron, etobenzanid, fenoxaprop-(-P-ethyl), fentrazamide, flamprop(-isopropyl), flamprop(-isopropyl-L), flamprop(-methyl), flazasulfuron, florasulam, fluazifop(-P-butyl), fluazolate, flucarbazone(-sodium), flufenacet, flufenpyr flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-butoxypropyl, -meptyl), flurprimidol, flurtamone, fluthiacet(-methyl), fluthiamide, fomesafen, foramsulfuron, glufosinate(-ammonium), glyphosate-(-isopropylammonium), halosafen, haloxyfop(-ethoxyethyl-P-methyl), haloxyfop(-ethoxyethyl, -P-methyl), hexazinone, imazamethabenz-(-methyl), imazamethapyr, imazamox, imazapic, imazapyr, imazaquin, imazethapyr, imazosulfuron, iodosulfuron(-methyl, -sodium), ioxynil, isopropalin, isoproturon, isouron, isoxaben, isoxachlortole, isoxaflutole, isoxapyrifop, ketospiradox, lactofen, lenacil, linuron, MCPA, mecoprop, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, penoxysulam, pentoxazone, pethoxamide, phenmedipham, picolinafen, piperophos, pretilachlor, primisulfuron(-methyl), profluazol, profoxydim, prometryn, propachlor, propanil, propaquizafop, propisochlor, propoxycarbazone(-sodium), propyzamide, prosulfocarb, prosulfuron, pyraflufen(-ethyl), pyrazogyl, pyrazolate, pyrazosulfuron(-ethyl), pyrazoxyfen, pyribenzoxim, pyributicarb, pyridate, pyridatol, pyriftalid, pyriminobac(-methyl), pyrithiobac(-sodium), quinchlorac, quinmerac, quinoclamine, quizalofop(-P-ethyl), quizalofop(-P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin, trifloxysulfuron, triflusulfuron (-methyl), and triflusulfuron.

Furthermore suitable for the mixtures are known safeners, for example

AD-67, BAS-145138, benoxacor, cloquintocet (-mexyl), cyometrinil, 2,4-D, DKA-24, dichlormid, dymron, fenclorim, fenchlorazol (-ethyl), flurazole, fluxofenim, furilazole, isoxadifen (-ethyl), MCPA, mecoprop (-P), mefenpyr (-diethyl), MG-191, oxabetrinil, PPG-1292, R-29148.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having certain properties ("traits") and which have been obtained by conventional breeding, by mutagenesis or by recombinant DNA techniques. They can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention—also in combination with other agro-chemical active compounds—, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects by toxins formed in the plants, in particular those formed in the plants by the genetic material from Bacillus thuringiensis (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of the plants to fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylurea, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the general formula (I) or the active compound mixtures according to the invention, where in addition to the good control of weed plants, the abovementioned synergistic effects with the transgenic plants or plant cultivars occur. The preferred ranges stated above for the active compounds or mixtures also apply to the treatment of these plants. Particular emphasis is given to the treatment of plants with the compounds or mixtures specifically mentioned in the present text.

The following examples show the preparation and use of the active compounds according to the invention:

PREPARATION EXAMPLES

Example 1

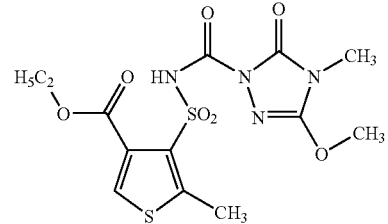

0.45 g (2.19 mmol) of 5-methoxy-4-methyl-2-phenoxycarbonyl-2,4-dihydro-3H-1,2,4-triazol-3-one is dissolved in 50 ml of acetonitrile and, at room temperature (about 20° C.), mixed with stirring, a little at a time, with 0.60 g (2.41 mmol) of 4-ethoxycarbonyl-2-methyl-thiophene-3-sulfonamide and with 0.37 g (2.41 mmol) of 1,8-diazabicyclo-[5.4.0]-undec-7-ene (DBU). The reaction mixture is stirred at room temperature for 12 hours and then concentrated under reduced pressure. The residue is taken up in methylene chloride and washed successively with 1N hydrochloric acid and with water, dried with sodium sulphate and filtered. The filtrate is concentrated under reduced pressure, the residue is digested with isopropanol and the resulting crystalline product is isolated by filtration with suction.

This gives 0.60 g (68% of theory) of ethyl 4-[[[(3-methoxy-4-methyl-5-oxo-1H-1,2,4-triazol-1-yl)carbonyl]amino]sulfonyl]-5-methyl-3-thiophenecarboxylate as a pale yellow solid of melting point 176° C.

The sodium salt of the compound prepared according to Example 1 can be prepared, for example, as follows:

1.0 g (2.5 mmol) of ethyl 4-[[[(3-methoxy-4-methyl-5-oxo-1H-1,2,4-triazol-1-yl)carbonyl]amino]sulfonyl]-5-methyl-3-thiophenecarboxylate are taken up in 25 ml of methylene chloride, and 0.10 g (2.5 mmol) of sodium hydroxide (micropellets) are added. The mixture is stirred at room temperature (or 20° C.) for 15 hours. The crystalline product is then isolated by filtration with suction.

This gives 1.0 g of ethyl 4-[[[(3-methoxy-4-methyl-5-oxo-1H-1,2,4-triazol-1-yl)carbonyl]amino]sulfonyl]-5-methyl-3-thiophenecarboxylate sodium salt of melting point 220° C.

Analogously to Example 1, and in accordance with the general description of the preparation process according to the invention, it is also possible to prepare, for example, the compounds of the general formula (I) listed in table 1 below.

TABLE 1

Examples of the compounds of the formula (I)

| Ex. No. | Q¹ | Q² | R¹ | R² | R³ | R⁴ | Melting point (°C.) |
|---|---|---|---|---|---|---|---|
| 2 | O | O | CH₃ | CH₃ | OCH₃ | CH₃ | 229 (Na-Salz) |
| 3 | O | O | CH₃ | CH₃ | R³ + R⁴: —S(CH₂)₂— | | 204 |
| 4 | O | O | CH₃ | CH₃ | R³ + R⁴: —O(CH₂)₂— | | 225 |
| 5 | O | O | CH₃ | CH₃ | R³ + R⁴: —S(CH₂)₃— | | 182 |
| 6 | O | O | CH₃ | CH₃ | R³ + R⁴: —O(CH₂)₃— | | 239 |
| 7 | O | O | CH₃ | CH₃ | R³ + R⁴ —N(CH₃)—(CH₂)₃— | | 219 |
| 8 | O | O | CH₃ | CH₃ | O-cyclohexyl | CH₃ | 163 |
| 9 | O | O | CH₃ | CH₃ | O-CH₂-CCl₃ | CH₃ | 170 |
| 10 | O | O | CH₃ | CH₃ | O-CH₂-CH₂-O-CH₃ | CH₃ | 154 |
| 11 | O | O | CH₃ | CH₃ | O-CH₂-phenyl | CH₃ | 165 |
| 12 | O | O | CH₃ | CH₃ | R³ + R⁴: —OCH₂—C(CH₃)₂—CH₂— | | 220 |
| 13 | O | O | CH₃ | CH₃ | O-phenyl | CH₃ | 203 |

TABLE 1-continued

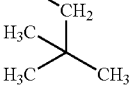

Examples of the compounds of the formula (I)

| Ex. No. | Q¹ | Q² | R¹ | R² | R³ | R⁴ | Melting point (°C.) |
|---|---|---|---|---|---|---|---|
| 14 | O | O | CH₃ | CH₃ | 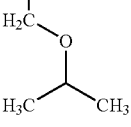 | CH₃ | 143 |
| 15 | O | O | CH₃ | CH₃ | C₃H₇-n | CH₃ | 154 |
| 16 | O | O | CH₃ | CH₃ | C₃H₇-i | CH₃ | 155 |
| 17 | O | O | CH₃ | CH₃ | C₄H₉-s | CH₃ | 156 |
| 18 | O | O | CH₃ | CH₃ | CH₂OCH₃ | CH₃ | 157 |
| 19 | O | O | CH₃ | CH₃ |  | CH₃ | 114 |
| 20 | O | O | CH₃ | CH₃ | SC₂H₅ | CH₃ | 162 |
| 21 | O | O | CH₃ | CH₃ | C₄H₉-t | CH₃ | 99 |
| 22 | O | O | CH₃ | CH₃ | 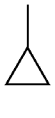 | CH₃ | 180 |
| 23 | O | O | CH₃ | CH₃ | CH₃ | C₂H₅ | 117 |
| 24 | O | O | CH₃ | CH₃ |  | C₃H₇-n | 151 |
| 25 | O | O | CH₃ | CH₃ | C₂H₅ | C₂H₅ | 147 |
| 26 | O | O | CH₃ | CH₃ | C₃H₇-n | C₂H₅ | 146 |
| 28 | O | O | CH₃ | CH₃ |  | C₂H₅ | 150 |
| 29 | O | O | CH₃ | CH₃ | CH₃ | C₃H₇-n | 135 |
| 30 | O | O | CH₃ | CH₃ | CH₃ | C₃H₇-i | 147 |
| 31 | O | O | CH₃ | CH₃ | C₂H₅ | C₃H₇-n | 159 |
| 32 | O | O | CH₃ | CH₃ | C₂H₅ | C₃H₇-i | 142 |
| 33 | O | O | CH₃ | CH₃ | C₃H₇-n | C₃H₇-n | 103 |
| 34 | O | O | CH₃ | CH₃ | C₃H₇-i | C₃H₇-n | 116 |
| 35 | O | O | CH₃ | CH₃ | C₃H₇-i | C₃H₇-i | 121 |
| 36 | O | O | CH₃ | CH₃ |  | C₃H₇-i | 126 |

TABLE 1-continued

Examples of the compounds of the formula (I)

| Ex. No. | Q¹ | Q² | R¹ | R² | R³ | R⁴ | Melting point (°C.) |
|---|---|---|---|---|---|---|---|
| 37 | O | O | CH₃ | CH₃ | C₃H₇-n | C₃H₇-i | 120 |
| 38 | O | O | CH₃ | CH₃ | OC₂H₅ | C₂H₅ | 124 |
| 39 | O | O | CH₃ | CH₃ | C₂H₅ | OC₂H₅ | 183 |
| 40 | O | O | CH₃ | CH₃ | Br | CH₃ | 189 |
| 41 | O | O | CH₃ | CH₃ | OCH₂CF₃ | CH₃ | 197 |
| 42 | O | O | CH₃ | CH₃ | C₃H₇-n | OCH₃ | 106 |
| 43 | O | O | CH₃ | CH₃ | OCH₂CF₃ | cyclopropyl | 117 |
| 44 | O | O | CH₃ | CH₃ | Br | cyclopropyl | 166 |
| 45 | O | O | CH₃ | CH₃ | CH₂OCH₃ | cyclopropyl | 185 |
| 46 | O | O | CH₃ | CH₃ | CH₃ | cyclopropyl | 206 |
| 47 | O | O | CH₃ | CH₃ | C₂H₅ | cyclopropyl | 175 |
| 48 | O | O | CH₃ | CH₃ | C₃H₇-n | cyclopropyl | 149 |
| 49 | O | O | CH₃ | CH₃ | C₃H₇-i | cyclopropyl | 214 |
| 50 | O | O | CH₃ | CH₃ | C₄H₉-t | cyclopropyl | 175 |
| 51 | O | O | CH₃ | CH₃ | C₄H₉-s | cyclopropyl | 205 |
| 52 | O | O | CH₃ | CH₃ | H | cyclopropyl | 201 |
| 53 | O | O | CH₃ | CH₃ | H | CH₃ | 170 |
| 54 | O | O | CH₃ | CH₃ | CH₃ | N(CH₃)₂ | 166 |
| 55 | O | O | C₂H₅ | CH₃ | OC₂H₅ | CH₃ | 172 |
| 56 | O | O | C₂H₅ | CH₃ | OCH₃ | cyclopropyl | 173 |

TABLE 1-continued

(I)

Examples of the compounds of the formula (I)

| Ex. No. | Q¹ | Q² | R¹ | R² | R³ | R⁴ | Melting point (° C.) |
|---|---|---|---|---|---|---|---|
| 57 | S | O | CH₃ | CH₃ | OCH₃ | CH₃ | 159 |
| 58 | S | O | CH₃ | CH₃ | OC₂H₅ | CH₃ | 133 |
| 59 | S | O | CH₃ | CH₃ | OC₃H₇-n | CH₃ | 60 |
| 60 | S | O | CH₃ | CH₃ | OC₃H₇i | CH₃ | 182 |
| 61 | S | O | CH₃ | CH₃ | OCH₃ | cyclopropyl | 201 |
| 62 | S | O | CH₃ | CH₃ | OC₂H₅ | cyclopropyl | 181 |
| 63 | S | O | CH₃ | CH₃ | OC₃H₇-n | cyclopropyl | 137 |
| 64 | S | O | CH₃ | CH₃ | cyclopropyl | cyclopropyl | 127 |
| 65 | S | O | CH₃ | CH₃ | CH₃ | CH₃ | 147 |
| 66 | S | O | CH₃ | CH₃ | C₂H₅ | CH₃ | 117 |
| 67 | S | O | CH₃ | CH₃ | SCH₃ | CH₃ | 138 |
| 68 | O | O | C₃H₇-i | CH₃ | OCH₃ | CH₃ | 190 |
| 69 | O | O | C₃H₇-i | CH₃ | OC₂H₅ | CH₃ | 193 |
| 70 | O | O | C₃H₇-i | CH₃ | OC₃H₇-n | CH₃ | 189 |
| 71 | O | O | C₃H₇-i | CH₃ | OC₃H₇-i | CH₃ | 184 |
| 72 | O | O | C₃H₇-i | CH₃ | OCH₃ | cyclopropyl | 189 |
| 73 | O | O | C₃H₇-i | CH₃ | OC₂H₅ | cyclopropyl | 115 |
| 74 | O | O | C₃H₇-i | CH₃ | OC₃H₇-n | cyclopropyl | 127 |
| 75 | O | O | C₃H₇-i | CH₃ | OC₃H₇-i | cyclopropyl | 251 |
| 76 | O | O | C₃H₇-i | CH₃ | cyclopropyl | cyclopropyl | 117 |
| 77 | O | O | C₃H₇-i | CH₃ | SCH₃ | CH₃ | 185 |
| 78 | O | O | C₃H₇-n | CH₃ | OCH₃ | CH₃ | 161 |
| 79 | O | O | C₃H₇-n | CH₃ | OC₂H₅ | CH₃ | 95 |
| 80 | O | O | C₃H₇-n | CH₃ | OC₃H₇-n | CH₃ | 156 |
| 81 | O | O | C₃H₇-n | CH₃ | OC₃H₇-i | CH₃ | 197 |

TABLE 1-continued

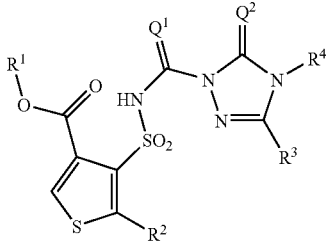

(I)

Examples of the compounds of the formula (I)

| Ex. No. | Q¹ | Q² | R¹ | R² | R³ | R⁴ | Melting point (° C.) |
|---|---|---|---|---|---|---|---|
| 82 | O | O | C₃H₇-n | CH₃ | OCH₃ | cyclopropyl | 169 |
| 83 | O | O | C₃H₇-n | CH₃ | OC₂H₅ | cyclopropyl | 150 |
| 84 | O | O | C₃H₇-n | CH₃ | OC₃H₇-n | cyclopropyl | 88 |
| 85 | O | O | C₃H₇-n | CH₃ | OC₃H₇-i | cyclopropyl | 95 |
| 86 | O | O | C₃H₇-n | CH₃ | cyclopropyl | cyclopropyl | 192 |
| 87 | O | O | C₃H₇-n | CH₃ | C₂H₅ | CH₃ | 110 |
| 88 | O | O | C₃H₇-n | CH₃ | SCH₃ | CH₃ | 188 |
| 89 | O | O | C₃H₇-i | CH₃ | R³ + R⁴: —S(CH₂)₂— | | 194 |
| 90 | O | O | C₃H₇-i | CH₃ | R³ + R⁴: —O(CH₂)₂— | | 188 |
| 91 | O | O | C₃H₇-i | CH₃ | CH₂OCH₃ | CH₃ | 122 |
| 92 | O | O | C₃H₇-i | CH₃ | R³ + R⁴: —OCH₂—C(CH₃)₂—CH₂— | | 205 |
| 93 | O | O | C₃H₇-i | CH₃ | (cyclohexyl-OCH₃) | CH₃ | 183 |
| 94 | O | O | C₃H₇-i | CH₃ | CH₃OCH₂CH(OCH₃)— | CH₃ | 54 |
| 95 | O | O | C₃H₇-i | CH₃ | CH₃OCH₂-C₆H₅— | CH₃ | 159 |

TABLE 1-continued

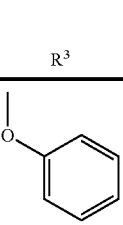

(I)

Examples of the compounds of the formula (I)

| Ex. No. | Q¹ | Q² | R¹ | R² | R³ | R⁴ | Melting point (° C.) |
|---|---|---|---|---|---|---|---|
| 96 | O | O | $C_3H_7$-i | $CH_3$ | 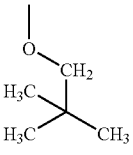 | $CH_3$ | 208 |
| 97 | O | O | $C_3H_7$-i | $CH_3$ |  | $CH_3$ | 115 |
| 98 | O | O | $C_3H_7$-i | $CH_3$ | $C_3H_7$-n | $CH_3$ | 105 |
| 99 | O | O | $C_3H_7$-i | $CH_3$ | $C_3H_7$-i | $CH_3$ | 106 |
| 100 | O | O | $C_3H_7$-i | $CH_3$ | $C_4H_9$-s | $CH_3$ | 103 |
| 101 | O | O | $C_3H_7$-i | $CH_3$ | $SC_2H_5$ | $CH_3$ | 113 |
| 102 | O | O | $C_3H_7$-i | $CH_3$ | $C_4H_9$-t | $CH_3$ | 131 |
| 103 | O | O | $C_3H_7$-i | $CH_3$ |  | $CH_3$ | 159 |
| 104 | O | O | $C_3H_7$-i | $CH_3$ | $CH_3$ | $C_3H_7$-i | 165 |
| 105 | S | O | $C_3H_7$-i | $CH_3$ | $OCH_3$ | $CH_3$ | 145 |
| 106 | S | O | $C_3H_7$-i | $CH_3$ | $OC_2H_5$ | $CH_3$ | 175 |
| 107 | S | O | $C_3H_7$-i | $CH_3$ | $OC_3H_7$-n | $CH_3$ | 166 |
| 108 | S | O | $C_3H_7$-i | $CH_3$ | $OC_3H_7$-i | $CH_3$ | 168 |
| 109 | S | O | $C_3H_7$-i | $CH_3$ | $OCH_3$ |  | 137 |
| 110 | S | O | $C_3H_7$-i | $CH_3$ | $OC_2H_5$ |  | 150 |
| 111 | S | O | $C_3H_7$-i | $CH_3$ | $OC_3H_7$-n |  | 136 |
| 112 | S | O | $C_3H_7$-n | $CH_3$ | $OCH_3$ | $CH_3$ | 137 |
| 113 | S | O | $C_3H_7$-n | $CH_3$ | $OC_2H_5$ | $CH_3$ | 160 |
| 114 | S | O | $C_3H_7$-n | $CH_3$ | $OC_3H_7$-n | $CH_3$ | 160 |
| 115 | O | O | $C_3H_7$-i | $CH_3$ | $OC_2H_5$ | $C_2H_5$ | 123 |
| 116 | O | O | $C_3H_7$-i | $CH_3$ | $C_2H_5$ | $OC_2H_5$ | 132 |
| 117 | O | O | $C_3H_7$-i | $CH_3$ | $OCH_2CF_3$ | $CH_3$ | 188 |
| 118 | O | O | $C_3H_7$-i | $CH_3$ | $C_3H_7$-n | $OCH_3$ | 245 |
| 119 | O | O | $C_3H_7$-i | $CH_3$ | $OCH_2CF_3$ |  | 255 |

TABLE 1-continued

Examples of the compounds of the formula (I)

| Ex. No. | Q¹ | Q² | R¹ | R² | R³ | R⁴ | Melting point (° C.) |
|---|---|---|---|---|---|---|---|
| 120 | O | O | $C_3H_7$-i | $CH_3$ | $CH_2OCH_3$ |  | 164 |
| 121 | S | O | $C_3H_7$-n | $CH_3$ | $OC_3H_7$-i | $CH_3$ | 172 |
| 122 | S | O | $C_3H_7$-n | $CH_3$ | $OCH_3$ |  | 140 |
| 123 | S | O | $C_3H_7$-n | $CH_3$ | $OC_2H_5$ |  | 139 |
| 124 | S | O | $C_3H_7$-n | $CH_3$ | $OC_3H_7$-n |  | 219 |
| 125 | S | O | $C_3H_7$-n | $CH_3$ | $OC_3H_7$-i |  | 120 |
| 126 | S | O | $CH_3$ | $CH_3$ | $OC_3H_7$-i |  | 144 |
| 127 | O | O | $C_3H_7$-i | $CH_3$ | Br |  | 156 |
| 128 | O | O | $C_3H_7$-i | $CH_3$ | $C_2H_5$ |  | 143 |
| 129 | O | O | $C_3H_7$-i | $CH_3$ | $C_3H_7$-i |  | 160 |
| 130 | O | O | $C_3H_7$-i | $CH_3$ | H |  | 183 |
| 131 | O | O | $C_3H_7$-i | $CH_3$ | H | $CH_3$ | 167 |
| 132 | S | O | $C_2H_5$ | $CH_3$ | $OCH_3$ | $CH_3$ | 165 |
| 133 | S | O | $C_2H_5$ | $CH_3$ | $OC_2H_5$ | $CH_3$ | 158 |
| 134 | S | O | $C_2H_5$ | $CH_3$ | $OC_3H_7$-n | $CH_3$ | 150 |
| 135 | S | O | $C_2H_5$ | $CH_3$ | $OC_3H_7$-i | $CH_3$ | 176 |
| 136 | S | O | $C_2H_5$ | $CH_3$ | $OCH_3$ |  | 159 |
| 137 | S | O | $C_2H_5$ | $CH_3$ | $OC_2H_5$ |  | 162 |

TABLE 1-continued

(I)

Examples of the compounds of the formula (I)

| Ex. No. | Q¹ | Q² | R¹ | R² | R³ | R⁴ | Melting point (°C.) |
|---|---|---|---|---|---|---|---|
| 138 | S | O | $C_2H_5$ | $CH_3$ | $OC_3H_7$-n |  | 156 |
| 139 | S | O | $C_2H_5$ | $CH_3$ | $OC_3H_7$-i | 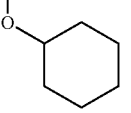 | 135 |
| 140 | O | O | $C_2H_5$ | $CH_3$ | R³ + R⁴: —S(CH₂)₂— | | 189 |
| 141 | O | O | $C_2H_5$ | $CH_3$ | R³ + R⁴: —S(CH₂)₃— | | 181 |
| 142 | O | O | $C_2H_5$ | $CH_3$ | R³ + R⁴: —OCH₂—C(CH₃)₂—CH₂— | | 212 |
| 143 | O | O | $C_2H_5$ | $CH_3$ | 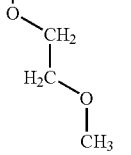 | $CH_3$ | 174 |
| 144 | O | O | $C_2H_5$ | $CH_3$ | $CH_2OCH_3$ | $CH_3$ | 116 |
| 145 | O | O | $C_2H_5$ | $CH_3$ | 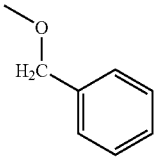 | $CH_3$ | 131 |
| 146 | O | O | $C_2H_5$ | $CH_3$ | 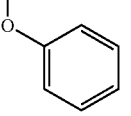 | $CH_3$ | 171 |
| 147 | O | O | $C_2H_5$ | $CH_3$ |  | $CH_3$ | 210 |
| 148 | O | O | $C_2H_5$ | $CH_3$ | $C_3H_7$-i | $CH_3$ | 175 |
| 149 | O | O | $C_2H_5$ | $CH_3$ | $SC_2H_5$ | $CH_3$ | 131 |
| 150 | O | O | $C_2H_5$ | $CH_3$ | $C_4H_9$-t | $CH_3$ | 129 |
| 151 | O | O | $C_2H_5$ | $CH_3$ | △ | $CH_3$ | 195 |

TABLE 1-continued

Examples of the compounds of the formula (I)

| Ex. No. | Q¹ | Q² | R¹ | R² | R³ | R⁴ | Melting point (° C.) |
|---|---|---|---|---|---|---|---|
| 152 | O | O | $C_2H_5$ | $CH_3$ | $CH_3$ | $C_2H_5$ | 140 |
| 153 | O | O | $C_2H_5$ | $CH_3$ |  | $C_3H_7$-n | 118 |
| 154 | O | O | $C_2H_5$ | $CH_3$ | $C_2H_5$ | $C_2H_5$ | 117 |
| 155 | O | O | $C_2H_5$ | $CH_3$ | $C_3H_7$-n | $C_2H_5$ | 165 |
| 156 | O | O | $C_2H_5$ | $CH_3$ | $C_3H_7$-i | $C_2H_5$ | 136 |
| 157 | O | O | $C_2H_5$ | $CH_3$ |  | $C_2H_5$ | 148 |
| 158 | O | O | $C_2H_5$ | $CH_3$ | $CH_3$ | $C_3H_7$-n | 135 |
| 159 | O | O | $C_2H_5$ | $CH_3$ | $CH_3$ | $C_3H_7$-i | 135 |
| 160 | O | O | $C_2H_5$ | $CH_3$ | $C_2H_5$ | $C_3H_7$-i | 142 |
| 161 | O | O | $C_2H_5$ | $CH_3$ |  | $C_3H_7$-i | 147 |
| 162 | O | O | $C_2H_5$ | $CH_3$ | $OC_2H_5$ | $C_2H_5$ | 127 |
| 163 | O | O | $C_2H_5$ | $CH_3$ | $C_2H_5$ | $OC_2H_5$ | 145 |
| 164 | O | O | $C_2H_5$ | $CH_3$ | $OCH_2CF_3$ | $CH_3$ | 175 |
| 165 | O | O | $C_2H_5$ | $CH_3$ | $C_3H_7$-n | $OCH_3$ | 112 |
| 166 | O | O | $C_2H_5$ | $CH_3$ | $OCH_2CF_3$ |  | 147 |
| 167 | O | O | $C_2H_5$ | $CH_3$ | $CH_2OCH_3$ |  | 147 |
| 168 | O | O | $C_2H_5$ | $CH_3$ | $CH_3$ |  | 152 |
| 169 | O | O | $C_2H_5$ | $CH_3$ | $C_2H_5$ |  | 159 |
| 170 | O | O | $C_2H_5$ | $CH_3$ | $C_3H_7$-n |  | 129 |
| 171 | O | O | $C_2H_5$ | $CH_3$ | $C_3H_7$-i |  | 158 |
| 172 | O | O | $C_2H_5$ | $CH_3$ | $C_4H_9$-t |  | 164 |

TABLE 1-continued
Examples of the compounds of the formula (I)
| Ex. No. | Q¹ | Q² | R¹ | R² | R³ | R⁴ | Melting point (° C.) |
|---|---|---|---|---|---|---|---|
| 173 | O | O | $C_2H_5$ | $CH_3$ | $C_4H_9$-s |  | 149 |
| 174 | O | O | $C_2H_5$ | $CH_3$ | H |  | 184 |
| 175 | O | O | $C_2H_5$ | $CH_3$ | H | $CH_3$ | 170 |
| 176 | O | O | $C_2H_5$ | $CH_3$ | $CH_3$ | $N(CH_3)_2$ | 130 |
| 177 | O | O | $C_2H_5$ | $CH_3$ | $C_4H_9$-i |  | 147 |
| 178 | O | O | $C_2H_5$ | $CH_3$ | $C_4H_9$-n | 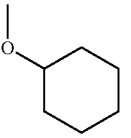 | 123 |
| 179 | O | O | $C_3H_7$-n | $CH_3$ | R³ + R⁴: —S(CH₂)₂— | | 182 |
| 180 | O | O | $C_3H_7$-n | $CH_3$ | R³ + R⁴: —S(CH₂)₃— | | 198 |
| 181 | O | O | $C_3H_7$-n | $CH_3$ | 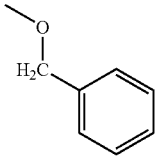 | $CH_3$ | 153 |
| 182 | O | O | $C_3H_7$-n | $CH_3$ | 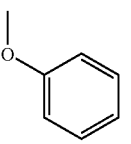 | $CH_3$ | 145 |
| 183 | O | O | $C_3H_7$-n | $CH_3$ | 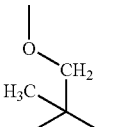 | $CH_3$ | 183 |
| 184 | O | O | $C_3H_7$-n | $CH_3$ |  | $CH_3$ | 170 |

TABLE 1-continued

Examples of the compounds of the formula (I)

| Ex. No. | Q¹ | Q² | R¹ | R² | R³ | R⁴ | Melting point (° C.) |
|---|---|---|---|---|---|---|---|
| 185 | O | O | C₃H₇-n | CH₃ | C₃H₇-n | CH₃ | 127 |
| 186 | O | O | C₃H₇-n | CH₃ | C₃H₇-i | CH₃ | 132 |
| 187 | O | O | C₃H₇-n | CH₃ | C₄H₉-s | CH₃ | 125 |
| 188 | O | O | C₃H₇-n | CH₃ | CH₂OCH₃ | CH₃ | 110 |
| 189 | O | O | C₃H₇-n | CH₃ | SC₂H₅ | CH₃ | 142 |
| 190 | O | O | C₃H₇-n | CH₃ | CH₃ | CH₃ | 145 |
| 191 | O | O | C₃H₇-n | CH₃ | CH₃ | C₃H₇-i | 174 |
| 192 | O | O | C₃H₇-n | CH₃ | C₂H₅ | C₃H₇-i | 120 |
| 193 | O | O | C₃H₇-n | CH₃ | OC₂H₅ | C₂H₅ | 121 |
| 194 | O | O | C₃H₇-n | CH₃ | C₂H₅ | OC₂H₅ | 120 |
| 195 | O | O | C₃H₇-n | CH₃ | OCH₂CF₃ | CH₃ | 140 |
| 196 | O | O | C₃H₇-n | CH₃ | C₃H₇-n | OCH₃ | 112 |
| 197 | O | O | C₃H₇-n | CH₃ | OCH₂CF₃ |  | 122 |
| 198 | O | O | C₃H₇-n | CH₃ | CH₂OCH₃ |  | 117 |
| 199 | O | O | C₃H₇-n | CH₃ | C₂H₅ |  | 180 |
| 200 | O | O | C₃H₇-n | CH₃ | C₃H₇-i |  | 183 |
| 201 | O | O | C₃H₇-n | CH₃ | H |  | 197 |
| 202 | O | O | C₃H₇-n | CH₃ | H | CH₃ | 125 |
| 203 | O | O | C₂H₅ | CH₃ | OC₃H₇-n | CH₃ | 139 |
| 204 | O | O | C₂H₅ | CH₃ | OC₃H₇-i | CH₃ | 180 |
| 205 | O | O | C₂H₅ | CH₃ | OC₂H₅ |  | 140 |
| 206 | O | O | C₂H₅ | CH₃ | OC₃H₇-n |  | 145 |
| 207 | O | O | C₂H₅ | CH₃ | OC₃H₇-i |  | 160 |
| 208 | O | O | C₂H₅ | CH₃ |  |  | 171 |
| 209 | O | O | C₂H₅ | CH₃ | CH₃ | CH₃ | 155 |
| 210 | O | O | C₂H₅ | CH₃ | C₂H₅ | CH₃ | 107 |

TABLE 1-continued

(I)

Examples of the compounds of the formula (I)

| Ex. No. | $Q^1$ | $Q^2$ | $R^1$ | $R^2$ | $R^3$ | $R^4$ | Melting point (° C.) |
|---|---|---|---|---|---|---|---|
| 211 | O | O | $C_2H_5$ | $CH_3$ | $SCH_3$ | $CH_3$ | 156 |
| 212 | O | O | $C_3H_7$-i | $CH_3$ | $C_2H_5$ | $C_3H_7$-i | 251 |
| 213 | O | O | $CH_3$ | $C_2H_5$ | $OC_3H_7$-i |  | 152 |
| 214 | O | O | $CH_3$ | $C_2H_5$ | $SC_2H_5$ | $CH_3$ | 145 |
| 215 | O | O | $CH_3$ | $C_2H_5$ | $OC_2H_5$ | $C_2H_5$ | 138 |
| 216 | O | O | $CH_3$ | $C_2H_5$ | $C_2H_5$ | $OC_2H_5$ | 141 |
| 217 | O | O | $CH_3$ | $C_2H_5$ | $OCH_2CF_3$ | $CH_3$ | 163 |
| 218 | O | O | $CH_3$ | $C_2H_5$ | $C_3H_7$-n | $OCH_3$ | 105 |
| 219 | O | O | $CH_3$ | $C_2H_5$ | $OCH_2CF_3$ |  | 161 |
| 220 | O | O | $CH_3$ | $CH_3$ | $OCH_3$ | $CH_3$ | 146 (Triethyl-ammonium salt) |
| 221 | O | O | $CH_3$ | $C_2H_5$ | $OCH_3$ | $CH_3$ | 236 (Lithium salt) |
| 222 | O | O | $CH_3$ | $C_2H_5$ | $OCH_3$ | $CH_3$ | 154 (Triethyl-ammonium salt) |
| 223 | O | O | $CH_3$ | $C_2H_5$ | $OCH_3$ | $CH_3$ | 162 (N,N-dimethyl-pyridin-4-yl-ammonium salt) |
| 224 | O | O | $CH_3$ | $C_2H_5$ | $OCH_3$ | $CH_3$ | 150 (1-hydroxy-methyl-propyl-propyl-ammonium salt) |
| 225 | O | O | $CH_3$ | $CH_3$ | $OCH_3$ | $CH_3$ | 151 (Diethyl-ammonium salt) |
| 226 | O | O | $CH_3$ | $CH_3$ | $OCH_3$ | $CH_3$ | 115 (Pyrrolidinium salt) |
| 227 | O | O | $CH_3$ | $CH_3$ | $OCH_3$ | $CH_3$ | 159 (1-hydroxy methyl propyl ammonium salt) |

Use Examples

In the use examples, the following prior-art compounds (all known from WO-A-01/05788) are used for comparison:

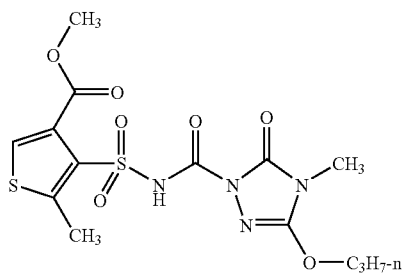

methyl 4-[[[(4,5-dihydro-4-methyl-5-oxo-3-n-propoxy-1H-1,2,4-triazol-1-yl)carbonyl]-amino]sulfonyl]-5-methyl-3-thiophenecarboxylate (A)

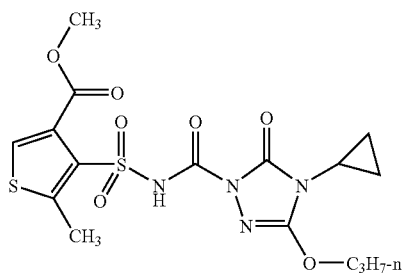

methyl 4-[[[(4-cyclopropyl-4,5-dihydro-5-oxo-3-n-propoxy-1H-1,2,4-triazol-1-yl)-carbonyl]amino]sulfonyl]-5-methyl-3-thiophenecarboxylate (B)

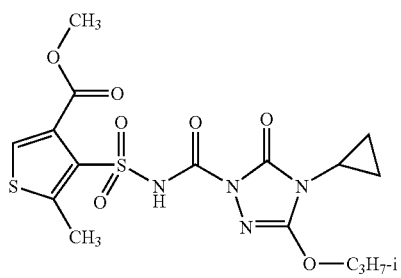

methyl 4-[[[(4-cyclopropyl-4,5-dihydro-5-oxo-3-isopropoxy-1H-1,2,4-triazol-1-yl)-carbonyl]amino]sulfonyl]-5-methyl-3-thiophenecarboxylate (C)

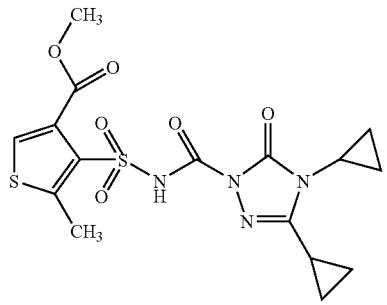

methyl 4-[[[(3,4-dicyclopropyl-4,5-dihydro-5-oxo-1H-1,2,4-triazol-1-yl)carbonyl]-amino]sulfonyl]-5-methyl-3-thiophenecarboxylate (D)

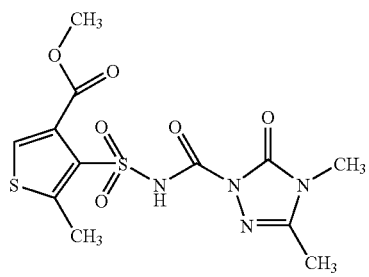

methyl 4-[[[(4,5-dihydro-3,4-dimethyl-5-oxo-1H-1,2,4-triazol-1-yl)carbonyl]-amino]sulfonyl]-5-methyl-3-thiophenecarboxylate (E)

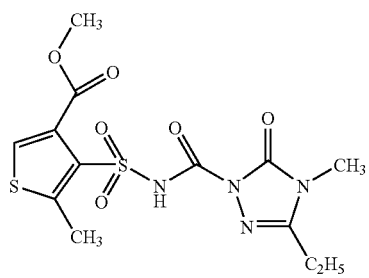

methyl 4-[[[(4,5-dihydro-3-ethyl-4-methyl-5-oxo-1H-1,2,4-triazol-1-yl)carbonyl]-amino]sulfonyl]-5-methyl-3-thiophenecarboxylate (F)

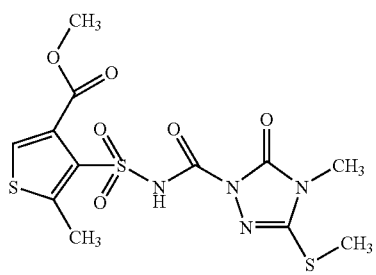

methyl 4-[[[(4,5-dihydro-4-methyl-3-methylthio-5-oxo-1H-1,2,4-triazol-1-yl)carbonyl]amino]sulfonyl]-5-methyl-3-thiophenecarboxylate (G)

Example A

Post-emergence Test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concetrate is diluted with water to the desired concentration.

Test plants of a height of 5-15 cm are sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:
0%=no effect (like untreated control)
100%=total destruction In this test, for example, the compounds of Preparation Examples 1, 15, 18, 20, 22, 39, 42, 45, 46, 47, 48, 55 and 56 show a considerably stronger activity against weeds and a substantially better compatibility with crop plants such as, for example, maize, oilseed rape and wheat than the known compounds (A) and (B).

Example B

Pre-emergence Test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concetrate is diluted with water to the desired concentration.

Seeds of the test plants are sown in normal soil. After 24 hours, the soil is sprayed with the preparation of active compound such that the particular amount of active compound desired is applied per unit area. The concentration of active compound in the spray liquor is chosen such that the particular amount of active compound desired is applied in 1000 litres of water per hectare.

After three weeks, the degree of damage to the plants is rated in % damage in comparison to the development of the untreated control. The figures denote:
0%=no effect (like untreated control)
100%=total destruction In this test, for example, the compounds of Preparation Examples 1, 15, 18, 20, 22, 38, 39, 41, 42, 43, 45, 46, 47, 48, 55 and 56 exhibit considerably stronger activity against weeds than the known compounds (A), (B), (C), (D), (E), (F) and (G), and substantially, they are tolerated well by crop plants, such as, for example, maize, soyabean and wheat.

TABLE A1

| | | Post-emergence-Test/greenhouse | | | | | | | |
|---|---|---|---|---|---|---|---|---|---|
| Compound of Preparation Example No. | application rate (gai/ha) | wheat | Avena fatua | Bromus | Echinochloa | Lolium | Datura | Viola | Xanthium |
| (B) | 15 | 30 | 50 | 50 | — | 60 | 80 | — | 50 |
| (A) | 15 | 0 | 30 | 50 | 60 | 30 | 50 | 30 | 70 |
| (56) | 15 | 0 | 90 | 90 | 95 | 90 | 90 | 95 | 95 |

TABLE A2

| | | Post-emergence-Test/greenhouse | | | | | | | |
|---|---|---|---|---|---|---|---|---|---|
| Compound of Preparation Example No. | application rate (gai/ha) | maize | Alopecurus | Bromus | Echinochloa | Lolium | Datura | Polygonum | Xanthium |
| (B) | 15 | 90 | 0 | 50 | — | 60 | 80 | 70 | 50 |
| (A) | 15 | 30 | 70 | 50 | 60 | 30 | 50 | 50 | 70 |
| (55) | 15 | 0 | 90 | 90 | 90 | 90 | 95 | 90 | 95 |

TABLE A3

Post-emergence-Test/greenhouse

| Compound of Preparation Example No. | application rate (gai/ha) | wheat | maize | *Echinochloa* | *Lolium* | *Datura* | *Polygonum* | *Viola* | *Xanthium* |
|---|---|---|---|---|---|---|---|---|---|
| (B) | 15 | 30 | 90 | — | 60 | 80 | 70 | — | 50 |
| (A) | 15 | 0 | 30 | 60 | 30 | 50 | 50 | 30 | 70 |
| (1) | 15 | 0 | 0 | 90 | 90 | 95 | 95 | 95 | 95 |

TABLE A4

Post-emergence-Test/greenhouse

| Compound of Preparation Example No. | application rate (gai/ha) | wheat | maize | *Alopecurus* | *Avena fatua* | *Bromus* | *Digitaria* | *Setaria* |
|---|---|---|---|---|---|---|---|---|
| (B) | 15 | 30 | 90 | 0 | 50 | 50 | 20 | 60 |
| (A) | 15 | 0 | 30 | 70 | 30 | 50 | 10 | 30 |
| (22) | 15 | 0 | 0 | 99 | 80 | 95 | 95 | 90 |

TABLE A5

Post-emergence-Test/greenhouse

| Compound of Preparation Example No. | application rate (gai/ha) | wheat | *Alopecurus* | *Bromus* | *Echinochloa* | *Viola* |
|---|---|---|---|---|---|---|
| (B) | 15 | 30 | 0 | 50 | — | — |
| (A) | 15 | 0 | 70 | 50 | 60 | 30 |
| (20) | 15 | 0 | 90 | 80 | 100 | 100 |

TABLE A6

Post-emergence-Test/greenhouse

| Compound of Preparation Example No. | application rate (gai/ha) | maize | *Alopecurus* | *Avena fatua* | *Bromus* | *Digitaria* | *Echinochloa* | *Lolium* | *Setaria* |
|---|---|---|---|---|---|---|---|---|---|
| (B) | 15 | 90 | 0 | 50 | 50 | 20 | — | 60 | 60 |
| (A) | 15 | 30 | 70 | 30 | 50 | 10 | 60 | 30 | 30 |
| (18) | 15 | 0 | 95 | 95 | 80 | 95 | 95 | 95 | 100 |

TABLE A7

Post-emergence-Test/greenhouse

| Compound of Preparation Example No. | application rate (gai/ha) | *Alopecurus* | *Avena fatua* | *Bromus* | *Digitaria* | *Echinochloa* | *Lolium* | *Setaria* |
|---|---|---|---|---|---|---|---|---|
| (B) | 15 | 0 | 50 | 50 | 20 | — | 60 | 60 |
| (A) | 15 | 70 | 30 | 50 | 10 | 60 | 30 | 30 |
| (15) | 15 | 95 | 90 | 80 | 100 | 90 | 80 | 90 |

TABLE A8

Post-emergence-Test/greenhouse

| Compound of Preparation Example No. | application rate (gai/ha) | *Avena fatua* | *Bromus* | *Digitaria* | *Echinochloa* | *Lolium* | *Setaria* |
|---|---|---|---|---|---|---|---|
| (A) | 15 | 30 | 50 | 10 | 60 | 30 | 30 |
| (39) | 15 | 90 | 95 | 95 | 100 | 95 | 95 |
| (45) | 15 | 90 | 90 | 100 | 100 | 95 | 90 |

TABLE A9

Post-emergence-Test/greenhouse

| Compound of Preparation Example No. | application rate (gai/ha) | rape | Alopecurus | Echinochloa | Lolium | Chenopodium |
|---|---|---|---|---|---|---|
| (A) | 15 | 95 | 70 | 60 | 30 | 80 |
| (42) | 15 | 0 | 90 | 90 | 90 | 95 |

TABLE A10

Post-emergence-Test/greenhouse

| Compound of Preparation Example No. | application rate (gai/ha) | Avena fatua | Digitaria | Echinochloa | Lolium | Setaria | Viola | Xanthium |
|---|---|---|---|---|---|---|---|---|
| (A) | 15 | 30 | 10 | 60 | 30 | 30 | 30 | 70 |
| (47) | 15 | 95 | 90 | 95 | 100 | 90 | 100 | — |
| (48) | 15 | 90 | 90 | 95 | 100 | 80 | 95 | 90 |

TABLE A11

Post-emergence-Test/greenhouse

| Compound of Preparation Example No. | application rate (gai/ha) | Avena fatua | Bromus | Digitaria | Lolium | Setaria | Xanthium |
|---|---|---|---|---|---|---|---|
| (B) | 15 | 50 | 50 | 20 | 60 | 60 | 50 |
| (39) | 15 | 90 | 95 | 95 | 95 | 95 | — |
| (45) | 15 | 90 | 90 | 100 | 95 | 90 | — |
| (47) | 15 | 95 | 80 | 90 | 100 | 90 | 80 |

TABLE A12

Post-emergence-Test/greenhouse

| Compound of Preparation Example No. | application rate (gai/ha) | Alopecurus | Avena fatua | Digitaria | Lolium | Xanthium |
|---|---|---|---|---|---|---|
| (B) | 15 | 0 | 50 | 20 | 60 | 50 |
| (46) | 15 | 80 | 80 | 90 | 95 | — |
| (48) | 15 | — | 90 | 90 | 100 | 90 |

TABLE B1

Pre-emergence-Test/greenhouse

| Compound of Preparation Example No. | application rate (gai/ha) | wheat | maize | Bromus | Lolium | Amaranthus | Matricaria | Solanum | Stellaria | Xanthium |
|---|---|---|---|---|---|---|---|---|---|---|
| (G) | 15 | 0 | 0 | — | 60 | 40 | 70 | 80 | 80 | 40 |
| (F) | 15 | 0 | 0 | 70 | 40 | 40 | 20 | 80 | 70 | 0 |
| (E) | 15 | 0 | 0 | 20 | 0 | 10 | 20 | 70 | 40 | 0 |
| (D) | 15 | 0 | 20 | 10 | 20 | 80 | 10 | 80 | 60 | 0 |
| (C) | 15 | 0 | 0 | 70 | 50 | 80 | 80 | — | 80 | 0 |
| (B) | 15 | 0 | 0 | 40 | 20 | 80 | 40 | 80 | 60 | 0 |
| (A) | 15 | 0 | 0 | 60 | 0 | — | 50 | 80 | 80 | 0 |
| (56) | 15 | 0 | 0 | 95 | 95 | 100 | 100 | 100 | 100 | 95 |
| (1) | 15 | 0 | 0 | 95 | 90 | 100 | 100 | 100 | 100 | 95 |

TABLE B2

Pre-emergence-Test/greenhouse

| Compound of Preparation Example No. | application rate (gai/ha) | wheat | maize | soybeans | Alopecurus | Lolium | Amaranthus | Matricaria | Solanum | Stellaria |
|---|---|---|---|---|---|---|---|---|---|---|
| (G) | 15 | 0 | 0 | 50 | — | 60 | 40 | 70 | 80 | 80 |
| (F) | 15 | 0 | 0 | 10 | 70 | 40 | 40 | 20 | 80 | 70 |
| (E) | 15 | 0 | 0 | 0 | 20 | 0 | 10 | 20 | 70 | 40 |
| (D) | 15 | 0 | 20 | 0 | 0 | 20 | 80 | 10 | 80 | 60 |
| (C) | 15 | 0 | 0 | 0 | 0 | 50 | 80 | 80 | — | 80 |
| (B) | 15 | 0 | 0 | 0 | 20 | 20 | 80 | 40 | 80 | 60 |
| (A) | 15 | 0 | 0 | 0 | 60 | 0 | — | 50 | 80 | 80 |
| (20) | 15 | 0 | 0 | 0 | 90 | 95 | 95 | 100 | 100 | 100 |

TABLE B3

Pre-emergence-Test/greenhouse

| Compound of Preparation Example No. | application rate (gai/ha) | wheat | maize | Alopecurus | Bromus | Lolium | Polygonum | Solanum | Stellaria | Xanthium |
|---|---|---|---|---|---|---|---|---|---|---|
| (G) | 15 | 0 | 0 | — | — | 60 | — | 80 | 80 | 40 |
| (F) | 15 | 0 | 0 | 70 | 70 | 40 | 50 | 80 | 70 | 0 |
| (E) | 15 | 0 | 0 | 20 | 20 | 0 | 20 | 70 | 40 | 0 |
| (D) | 15 | 0 | 20 | 0 | 10 | 20 | 10 | 80 | 60 | 0 |
| (C) | 15 | 0 | 0 | 0 | 70 | 50 | 60 | — | 80 | 0 |
| (B) | 15 | 0 | 0 | 20 | 40 | 20 | 50 | 80 | 60 | 0 |
| (A) | 15 | 0 | 0 | 60 | 60 | 0 | 0 | 80 | 80 | 0 |
| (55) | 15 | 0 | 0 | 95 | 95 | 90 | 95 | 100 | 100 | 95 |
| (22) | 15 | 0 | 0 | 95 | 100 | 95 | 95 | 100 | 100 | — |
| (15) | 15 | 0 | 0 | 100 | 90 | 95 | 90 | 95 | 100 | 95 |

TABLE B4

Pre-emergence-Test/greenhouse

| Compound of Preparation Example No. | application rate (gai/ha) | wheat | maize | soybeans | Alopecurus | Setaria | Amaranthus | Matricaria | Stellaria |
|---|---|---|---|---|---|---|---|---|---|
| (G) | 15 | 0 | 0 | 50 | — | 70 | 40 | 70 | 80 |
| (F) | 15 | 0 | 0 | 10 | 70 | 30 | 40 | 20 | 70 |
| (E) | 15 | 0 | 0 | 0 | 20 | 20 | 10 | 20 | 40 |
| (D) | 15 | 0 | 20 | 0 | 0 | 10 | 80 | 10 | 60 |
| (C) | 15 | 0 | 0 | 0 | 0 | 50 | 80 | 80 | 80 |
| (B) | 15 | 0 | 0 | 0 | 20 | 40 | 80 | 40 | 60 |
| (A) | 15 | 0 | 0 | 0 | 60 | 0 | — | 50 | 80 |
| (18) | 15 | 0 | 0 | 0 | 95 | 95 | 95 | 100 | 95 |

TABLE B5

Pre-emergence-Test/greenhouse

| Compound of Preparation Example No. | application rate (gai/ha) | maize | soybeans | Lolium | Setaria | Amaranthus | Chenopodium | Solanum | Stellaria |
|---|---|---|---|---|---|---|---|---|---|
| (G) | 15 | 0 | 50 | 60 | 70 | 40 | 50 | 80 | 80 |
| (F) | 15 | 0 | 10 | 40 | 30 | 40 | 0 | 80 | 70 |
| (E) | 15 | 0 | 0 | 0 | 20 | 10 | 0 | 70 | 40 |
| (D) | 15 | 20 | 0 | 20 | 10 | 80 | 0 | 80 | 60 |
| (C) | 15 | 0 | 0 | 50 | 50 | 80 | 40 | — | 80 |
| (B) | 15 | 0 | 0 | 20 | 40 | 80 | 40 | 80 | 60 |
| (A) | 15 | 0 | 0 | 0 | 0 | — | 50 | 80 | 80 |
| (38) | 15 | 0 | 0 | 80 | 95 | 100 | 95 | 100 | 100 |

TABLE B6

Pre-emergence-Test/greenhouse

| Compound of Preparation Example No. | application rate (gai/ha) | wheat | maize | Alopecurus | Setaria | Amaranthus | Chenopodium | Solanum | Stellaria |
|---|---|---|---|---|---|---|---|---|---|
| (G) | 15 | 0 | 0 | — | 70 | 40 | 50 | 80 | 80 |
| (F) | 15 | 0 | 0 | 70 | 30 | 40 | 0 | 80 | 70 |
| (E) | 15 | 0 | 0 | 20 | 20 | 10 | 0 | 70 | 40 |
| (D) | 15 | 0 | 20 | 0 | 10 | 80 | 0 | 80 | 60 |
| (C) | 15 | 0 | 0 | 0 | 50 | 80 | 40 | — | 80 |
| (B) | 15 | 0 | 0 | 20 | 40 | 80 | 40 | 80 | 60 |
| (A) | 15 | 0 | 0 | 60 | 0 | — | 50 | 80 | 80 |
| (41) | 15 | 0 | 0 | 100 | 95 | 100 | 100 | 100 | 100 |

TABLE B7

Pre-emergence-Test/greenhouse

| Compound of Preparation Example No. | application rate (gai/ha) | wheat | Digitaria | Lolium | Setaria | Amaranthus | Solanum | Stellaria |
|---|---|---|---|---|---|---|---|---|
| (G) | 15 | 0 | 50 | 60 | 70 | 40 | 80 | 80 |
| (F) | 15 | 0 | 60 | 40 | 30 | 40 | 80 | 70 |
| (E) | 15 | 0 | 0 | 0 | 20 | 10 | 70 | 40 |
| (D) | 15 | 0 | 20 | 20 | 10 | 80 | 80 | 60 |
| (C) | 15 | 0 | 20 | 50 | 50 | 80 | — | 80 |
| (B) | 15 | 0 | 0 | 20 | 40 | 80 | 80 | 60 |
| (A) | 15 | 0 | 0 | 0 | 0 | — | 80 | 80 |
| (39) | 15 | 0 | 100 | 95 | 100 | 100 | 95 | 100 |

TABLE B8

Pre-emergence-Test/greenhouse

| Compound of Preparation Example No. | application rate (gai/ha) | wheat | maize | soybeans | Alopecurus | Lolium | Matricaria | Stellaria |
|---|---|---|---|---|---|---|---|---|
| (G) | 15 | 0 | 0 | 50 | — | 60 | 70 | 80 |
| (F) | 15 | 0 | 0 | 10 | 70 | 40 | 20 | 70 |
| (E) | 15 | 0 | 0 | 0 | 20 | 0 | 20 | 40 |
| (D) | 15 | 0 | 20 | 0 | 0 | 20 | 10 | 60 |
| (C) | 15 | 0 | 0 | 0 | 0 | 50 | 80 | 80 |
| (B) | 15 | 0 | 0 | 0 | 20 | 20 | 40 | 60 |
| (A) | 15 | 0 | 0 | 0 | 60 | 0 | 50 | 80 |
| (46) | 15 | 0 | 50 | 0 | 0 | 95 | 90 | 100 | 100 |

TABLE B9

Pre-emergence-Test/greenhouse

| Compound of Preparation Example No. | application rate (gai/ha) | Avena fatua | Lolium | Setaria | Amaranthus | Matricaria | Polygonum | Stellaria |
|---|---|---|---|---|---|---|---|---|
| (G) | 15 | 50 | 60 | 70 | 40 | 70 | 70 | 80 |
| (F) | 15 | 60 | 40 | 30 | 40 | 20 | 50 | 70 |
| (E) | 15 | 0 | 0 | 20 | 10 | 20 | 20 | 40 |
| (D) | 15 | 70 | 20 | 10 | 80 | 10 | 10 | 60 |
| (C) | 15 | 50 | 50 | 50 | 80 | 80 | 60 | 80 |
| (B) | 15 | 10 | 20 | 40 | 80 | 40 | 50 | 60 |
| (A) | 15 | 0 | 0 | 0 | — | 50 | 0 | 80 |
| (43) | 15 | — | 95 | 95 | 100 | 100 | 100 | 100 |
| (45) | 15 | 95 | 100 | 100 | 100 | 100 | 95 | 100 |
| (47) | 15 | 95 | 80 | 95 | 100 | 100 | 90 | 100 |
| (48) | 15 | 95 | 95 | — | 100 | 95 | 95 | 100 |

TABLE B10

Pre-emergence-Test/greenhouse

| Compound of Preparation Example No. | application rate (gai/ha) | Avena fatua | Bromus | Lolium | Setaria | Amaranthus | Galium | Stellaria |
|---|---|---|---|---|---|---|---|---|
| (G) | 15 | 50 | — | 60 | 70 | 40 | 30 | 80 |
| (F) | 15 | 60 | 70 | 40 | 30 | 40 | 10 | 70 |
| (E) | 15 | 0 | 20 | 0 | 20 | 10 | 0 | 40 |
| (D) | 15 | 70 | 10 | 20 | 10 | 80 | 0 | 60 |
| (C) | 15 | 50 | 70 | 50 | 50 | 80 | 70 | 80 |
| (B) | 15 | 10 | 40 | 20 | 40 | 80 | 20 | 60 |
| (A) | 15 | 0 | 60 | 0 | 0 | — | 10 | 80 |
| (42) | 15 | 90 | 95 | 95 | 95 | 100 | 100 | 100 |

The invention claimed is:

1. A compound of formula (I)

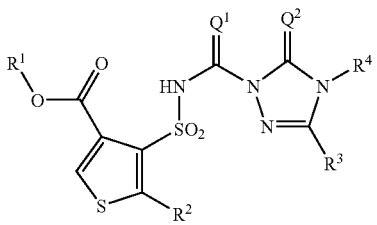

or salts thereof,
in which
$Q^1$ represents S,
$Q^2$ represents O,
$R^1$ represents optionally cyano-, halogen-, or $C_1$-$C_4$-alkoxy-substituted alkyl having 1 to 6 carbon atoms; represents optionally cyano- or halogen-substituted alkenyl or alkynyl having in each case 2 to 6 carbon atoms; represents optionally cyano-, halogen-, or $C_1$-$C_4$-alkyl-substituted cycloalkyl or cycloalkylalkyl having in each case 3 to 6 carbon atoms in the cycloalkyl group and, optionally, 1 to 4 carbon atoms in the alkyl moiety; represents optionally nitro-, cyano-, halogen-, $C_1$-$C_4$-alkyl-, or $C_1$-$C_4$-alkoxy-substituted aryl or arylalkyl having in each case 6 or 10 carbon atoms in the aryl group and, optionally, 1 to 4 carbon atoms in the alkyl moiety; or represents optionally nitro-, cyano-, halogen-, $C_1$-$C_4$-alkyl-, or $C_1$-$C_4$-alkoxy-substituted heterocyclyl or heterocyclylalkyl having in each case up to 6 carbon atoms and additionally 1 to 4 nitrogen atoms and/or 1 or 2 oxygen or sulphur atoms in the heterocyclyl group and, optionally, 1 to 4 carbon atoms in the alkyl moiety, $R^2$ represents hydrogen, cyano, nitro, or halogen; represents optionally, cyano-, halogen-, or $C_1$-$C_4$-alkoxy-substituted alkyl, alkoxy, alkoxycarbonyl, alkylthio, alkylsulfinyl, or alkylsulfonyl having in each case 1 to 6 carbon atoms in the alkyl group; or represents optionally cyano- or halogen-substituted alkenyl, alkynyl, alkenyloxy, or alkynyloxy having in each case 2 to 6 carbon atoms in the alkenyl or alkynyl group, $R^3$ represents hydrogen, hydroxyl, mercapto, amino, cyano, or halogen; represents optionally cyano-, halogen-, $C_1$-$C_4$-alkoxy-, $C_1$-$C_4$-alkyl-carbonyl-, or $C_1$-$C_4$-alkoxy-carbonyl-substituted alkyl having 1 to 6 carbon atoms; represents optionally fluorine-, chlorine-, and/or bromine-substituted alkenyl or alkynyl having in each case 2 to 6 carbon atoms; represents optionally cyano-, halogen-, $C_1$-$C_4$-alkoxy-, or $C_1$-$C_4$-alkoxy-carbonyl-substituted alkoxy, alkylthio, alkylamino, or alkylcarbonylamino having in each case 1 to 6 carbon atoms in the alkyl group; represents alkenyloxy, alkynyloxy, alkenylthio, alkynylthio, alkenylamino, or alkynylamino having in each case 3 to 6 carbon atoms in the alkenyl or alkynyl group; represents dialkylamino having in each case 1 to 4 carbon atoms in the alkyl groups; represents optionally methyl- and/or ethyl-substituted aziridino, pyrrolidino, piperidino, or morpholino; represents optionally fluorine-, chlorine-, bromine-, cyano-, and/or $C_1$-$C_4$-alkyl-substituted cycloalkyl, cycloalkenyl, cycloalkyloxy, cycloalkylthio, cycloalkylamino, cycloalkylalkyl, cycloalkylalkoxy, cycloalkylalkylthio, or cycloalkylalkylamino having in each case 3 to 6 carbon atoms in the cycloalkyl or cycloalkenyl group and, optionally, 1 to 4 carbon atoms in the alkyl moiety; or represents optionally fluorine-, chlorine-, bromine-, cyano-, nitro-, $C_1$-$C_4$-alkyl-, trifluoromethyl-, $C_1$-$C_4$-alkoxy- and/or $C_1$-$C_4$-alkoxy-carbonyl-substituted aryl, arylalkyl, aryloxy, arylalkoxy, arylthio, arylalkylthio, arylamino, or arylalkylamino having in each case 6 or 10 carbon atoms in the aryl group and, optionally, 1 to 4 carbon atoms in the alkyl moiety, and $R^4$ represents hydrogen, hydroxy, amino, or cyano; represents $C_2$-$C_{10}$-alkylideneamino; represents optionally fluorine-, chlorine-, bromine-, cyano-, $C_1$-$C_4$-alkoxy-, $C_1$-$C_4$-alkyl-carbonyl-, or $C_1$-$C_4$-alkoxy-carbonyl-substituted alkyl having 1 to 6 carbon atoms; represents optionally fluorine-, chlorine-, and/or bromine-substituted alkenyl or alkynyl having in each case 2 to 6 carbon atoms; represents optionally fluorine-, chlorine-, bromine-, cyano-, $C_1$-$C_4$-alkoxy-, or $C_1$-$C_4$-alkoxy-carbonyl-substituted alkoxy, alkylamino or alkylcarbonylamino having in each case 1 to 6 carbon atoms in the alkyl groups; represents alkenyloxy having 3 to 6 carbon atoms; represents dialkylamino having in each case 1 to 4 carbon atoms in the alkyl groups; represents optionally fluorine-, chlorine-, bromine-, cyano-, and/or $C_1$-$C_4$-alkyl-substituted cycloalkyl, cycloalkylamino, or cycloalkylalkyl having in each case 3 to 6 carbon atoms in the alkyl group and, optionally, 1 to 4 carbon atoms in the alkyl moiety; or represents optionally fluorine-, chlorine-, bromine-, cyano-, nitro-, $C_1$-$C_4$-alkyl-, trifluoromethyl-, and/or $C_1$-$C_4$-alkoxy-substituted aryl or arylalkyl having in each case 6 or 10 carbon atoms in the aryl group and, optionally, 1 to 4 carbon atoms in the alkyl moiety; or together with $R^3$ represents optionally branched and/or $C_1$-$C_4$-alkyl-substituted alkanediyl, oxaalkanediyl, thiaalkanediyl, or azaalkanediyl having 3 to 6 carbon atoms, wherein the oxa, thia, or aza components are positioned at the beginning, at the end, or within the alkanediyl group, except for methyl 4-[[[(4,5-dihydro-3-ethoxy-4-methyl-5-oxo-1H-1,2,4-triazol-1-yl)thioxocarbonyl]amino]sulfonyl]-5-fluoro-3-thiophenecarboxylate.

2. A compound according to claim 1 in which $R^1$ represents optionally cyano-, fluorine-, chlorine-, methoxy-, or ethoxy-substituted methyl, ethyl, n- or isoproyl, or n-, iso-, s-, or t-butyl; represents optionally cyano-, fluorine-, or chlorine-substituted propenyl, butenyl, propynyl, or butynyl; represents optionally cyano-, fluorine-, chlorine-, methyl-, or ethyl-substituted cyclopropyl, cyclobutyl, cyclopentyl, cyclohexyl, cyclopropylmethyl, cyclobutyl methyl, cyclopentylmethyl, or cyclohexylmethyl; represents optionally cyano-, fluorine-, chlorine-, methyl-, ethyl-, n- or isopropyl-, trifluoromethyl-, methoxy-, ethoxy-, n- or isopropoxy-, difluoromethoxy-, or trifluoromethoxy-substituted phenyl, phenylmethyl or phenylethyl; or represents optionally cyano-, fluorine-, chlorine-, bromine-, methyl-, ethyl-, n- or isopropyl-, methoxy-, ethoxy-, or n- or isopropoxy-substituted heterocyclyl or heterocyclylmethyl, where the heterocyclyl group is in each case selected from the group consisting of oxetanyl, thietanyl, furyl, tetrahydrofuryl, thienyl, and tetrahydrothienyl, $R^2$ represents hydrogen, cyano, fluorine, chlorine, or bromine; represents optionally cyano-, fluorine-, chlorine-, methoxy-, or ethoxy-substituted methyl, ethyl, n- or isopropyl, n-, iso-, s-, or t-butyl, methoxy, ethoxy, n- or isopropoxy, methoxycarbonyl, ethoxycarbonyl, n- or isopropoxycarbonyl, methylthio, ethylthio, n- or isopropylthio, methylsulfinyl, ethylsulfinyl, methylsulfonyl, or ethylsulfonyl; or represents optionally cyano-, fluorine-, or chlorine-substituted propenyl, butenyl, propynyl, butynyl, propenyloxy, butenyloxy, propynyloxy, or butynyloxy, $R^3$ represents hydrogen, hydroxy, mercapto, amino, cyano, fluorine, chlorine, or bromine; represents optionally fluorine-, chlorine-, cyano-, methoxy-, ethoxy-, n- or isopropoxy-, acetyl-, propionyl-, n- or isobutyroyl-, methoxycarbonyl-, ethoxycarbonyl-, or n- or isopropoxycarbonyl-substituted methyl, ethyl, n- or isopropyl, n-, iso-, s-, or t-butyl, n-, iso-, s-, or t-pentyl, or neopentyl; represents optionally fluorine-, chlorine-, and/or bromine-substituted ethenyl, propenyl, butenyl, ethynyl, propynyl, or butynyl; represents optionally fluorine-, chlorine-, cyano-, methoxy-, ethoxy-, n- or isopropoxy-, n-, iso-, s-, or t-butoxy-, methoxycarbonyl-, ethoxycarbonyl-, or n- or isopropoxycarbonyl-substituted methoxy, ethoxy, n- or isopropoxy, n-, iso-, s- or t-butoxy, n-, iso-, s-, or t-pentyloxy, neopentyloxy, methylthio, ethylthio, n- or isopropylthio, n-, iso-, s-, or t-butylthio, methylamino, ethylamino, n- or isopropylamino, n-, iso-, s-, or t-butylamino, acetylamino, or propionylamino; represents propenyloxy, butenyloxy, ethynyloxy, propynyloxy, butynyloxy, propenylthio, butenylthio, propynylthio, butynylthio, propenylamino, butenylamino, propynylamino, or butynylamino; represents dimethylamino, diethylamino, or dipropylamino; represents optionally fluorine-, chlorine-, methyl-, and/or ethyl-substituted cyclopropyl, cyclobutyl, cyclopentyl, cyclohexyl, cyclopentenyl, cyclohexenyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropyl methyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino, or cyclohexylmethylamino; or represents optionally fluorine-, chlorine-, bromine-, methyl-, trifluoromethyl-, methoxy-, or methoxycarbonyl-substituted phenyl, benzyl, phenoxy, benzyloxy, phenylthio, benzylthio, phenylamino, or benzylamino, and $R^4$ represents hydrogen, hydroxy, or amino; represents optionally fluorine-, chlorine-, cyano-, methoxy-, or ethoxy-substituted methyl, ethyl, n- or isopropyl, or n-, iso-, s-, or t-butyl; represents optionally fluorine-, chlorine-, and/or bromine-substituted ethenyl, propenyl, butenyl, propynyl, or butynyl; represents optionally fluorine-, chlorine-, cyano-, methoxy-, or ethoxy substituted methoxy, ethoxy, n- or isopropoxy, n-, iso-, s-, or t-butoxy, methylamino, ethylamino, n- or isopropylamino, or n-, iso-, s-, or t-butylamino; represents propenyloxy or butenyloxy; represents dimethylamino or diethylamino; represents optionally fluorine-, chlorine-, methyl-, and/or ethyl-substituted cyclopropyl, cyclobutyl, cyclopentyl, cyclohexyl, cyclopropylamino, cyclobutylamino, cyclopentylamino, cyclohexylamino, cyclopropylmethyl, cyclobutyl methyl, cyclopentylmethyl, or cyclohexylmethyl; or represents optionally fluorine-, chlorine-, methyl-, trifluoromethyl-, and/or methoxy-substituted phenyl or benzyl, or $R^3$ and $R^4$ together represent trimethylene (propane-1,3-diyl), 1-oxatrimethylene, 1-thiatrimethylene, 1-azatrimethylene, tetramethylene (butane-1,4-diyl), 1-oxatetramethylene, 1-thiatetramethylene, 1-azatetramethylene, or pentamethylene (pentane-1,5-diyl), each of which is optionally mono- to trisubstituted by methyl and/or ethyl, where position 1 is connected to the point of attachment of $R^3$.

3. A compound according to claim 1 in which $R^1$ represents optionally fluorine-, chlorine-, methoxy-, or ethoxy-substituted methyl, ethyl, or n- or isopropyl, $R^2$ represents fluorine, chlorine, or bromine; or represents optionally fluorine-, chlorine-, methoxy- or ethoxy-substituted methyl, ethyl, or n- or isopropyl, $R^3$ represents hydrogen, chlorine, or bromine; represents optionally fluorine-, chlorine-, methoxy-, ethoxy-, or n- or isopropoxy-substituted methyl, ethyl, n- or isopropyl, n-, iso-, s-, or t-butyl, n-, iso-, s-, or t-pentyl, or neopentyl; represents optionally fluorine- or chlorine-substituted ethenyl, propenyl, butenyl, propynyl, or butynyl; represents optionally fluorine-, chlorine-, methoxy-, ethoxy-, n- or isopropoxy-substituted methoxy, ethoxy, n- or isopropoxy, n-, iso-, s-, or t-butoxy, n-, iso-, s-, or t-pentyloxy, neopentyloxy, methylthio, ethylthio, n- or isopropylthio, n-, iso-, s-, or t-butylthio, methylamino, ethylamino, or n- or isopropylamino; represents propenyloxy, propynyloxy, propenylthio, propynylthio, propenylamino, or propynylamino; represents dimethylamino or diethylamino; represents optionally fluorine-, chlorine-, or methyl-substituted cyclopropyl, cyclopropyloxy, cyclopropylmethyl, cyclopropylmethoxy, cyclobutyloxy, cyclopentyloxy, or cyclohexyloxy; or represents optionally fluorine-, chlorine-, or methyl-substituted phenoxy or benzyloxy, and R⁴ represents optionally fluorine-, chlorine-, methoxy-, or ethoxy-substituted methyl, ethyl, or n- or isopropyl; represents optionally fluorine- or chlorine-substituted ethenyl, propenyl, or propynyl; represents optionally fluorine-, chlorine-, methoxy-, or ethoxy-substituted methoxy, ethoxy, or n- or isopropoxy; represents methylamino; or represents cyclopropyl, or R³ and R⁴ together represent trimethylene (propane-1,3-diyl), 1-oxatrimethylene, 1-thiatrimethylene, 1-azatrimethylene, tetramethylene (butane-1,4-diyl), 1-oxatetramethylene, 1-thiatetramethylene, 1-azatetramethylene, or pentamethylene (pentane-1,5-diyl), each of which is optionally mono- or disubstituted by methyl, where position 1 is connected to the point of attachment of R³.

4. A compound according to claim 3 in which R¹ represents methyl.

5. A compound according to claim 3 in which R¹ represents ethyl.

6. A compound according to claim 3 in which R¹ represents n-propyl.

7. A compound according to claim 3 in which R¹ represents isopropyl.

8. A compound according to claim 3 in which R³ and R⁴ together represent trimethylene (propane-1,3-diyl), 1-oxatrimethylene, 1-thiatrimethylene, 1-azatrimethylene, tetramethylene (butane-1,4-diyl), 1-oxatetramethylene, 1-thiatetramethylene, 1-azatetramethylene or pentamethylene (pentane-1,5-diyl), each of which is optionally mono- or disubstituted by methyl, where position 1 is connected to the point of attachment of R³.

9. A compound according to claim 3 in which R³ represents halogen- or $C_1$-$C_4$-alkoxy-substituted alkoxy having 1 to 6 carbon atoms.

10. A process for preparing a compound according to claim 1 comprising (a) reacting a substituted thiophene-3-sulphonamide of formula (II)

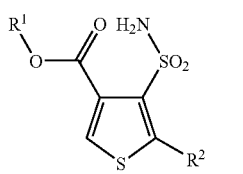

(II)

in which R¹ and R² are as defined for formula (I) of claim 1, with a substituted triazolin(ethi)one of formula (III)

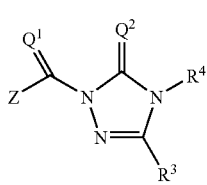

(III)

in which
Q¹, Q², Q³, and R⁴ are as defined for formula (I) of claim 1, and

Z represents halogen, alkoxy, aryloxy, or arylalkoxy, optionally in the presence of a reaction auxiliary and optionally in the presence of a diluent, or (b) reacting a substituted thiene-3-ylsulphonyl iso(thio)cyanate of formula (IV)

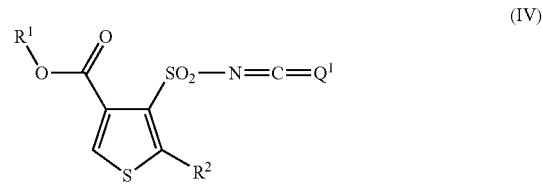

(IV)

in which Q¹, R¹, and R² are as defined for formula (I) of claim 1, with a triazolin(ethi)one of formula (V)

(V)

in which Q², R⁴, and R⁵ are as defined for formula (I) of claim 1, optionally in the presence of a reaction auxiliary and optionally in the presence of a diluent, or (c) reacting a substituted thiophene-3-sulphonyl chloride of formula (VI)

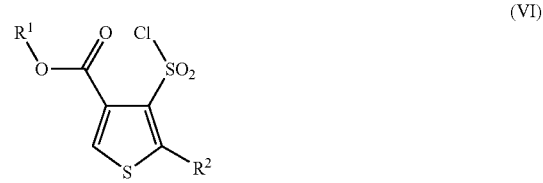

(VI)

in which R¹ and R² are as defined for formula (I) of claim 1, with a triazolin(ethi)one of formula (V)

(V)

in which Q², R⁴, and R⁵ are as defined for formula (I) of claim 1, and a metal (thio)cyanate of formula (VII)

M-Q¹-CN (VII)

in which $Q^1$ is as defined for formula (I) of claim 1, optionally in the presence of a reaction auxiliary and optionally in the presence of a diluent, or (d) reacting a substituted thiophene-3-sulphonyl chloride of formula (VI)

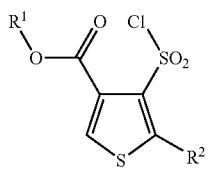
(VI)

in which $R^1$ and $R^2$ are as defined for formula (I) of claim 1, with a triazolin(ethi)one (thio)carboxamide of formula (VIII)

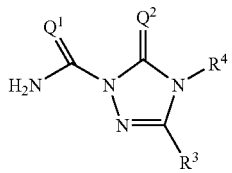
(VIII)

in which $Q^1$, $Q^2$, $R^3$, and $R^4$ are as defined for formula (I) of claim 1, optionally in the presence of a reaction auxiliary and optionally in the presence of a diluent, or (e) reacting a substituted thiene-3-ylsulphonylamino(thio)carbonyl compound of formula (IX)

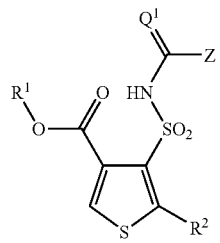
(IX)

in which $Q^1$, $R^1$, and $R^2$ are as defined for formula (I) of claim 1, and Z represents halogen, alkoxy, aryloxy, or arylalkoxy, with a triazolin(ethi)one of formula (V)

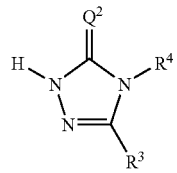
(V)

in which $Q^2$, $R^4$, and $R^5$ are as defined for formula (I) of claim 1, optionally in the presence of a reaction auxiliary and optionally in the presence of a diluent.

11. A process according to claim 10 additionally comprising converting a compound of formula (I) prepared according claim 10 to a salt thereof.

12. A herbicidal composition comprising a compound according to claim 1 and one or more extenders and/or surfactants.

* * * * *